US006455506B1

(12) United States Patent
Townsend et al.

(10) Patent No.: US 6,455,506 B1
(45) Date of Patent: Sep. 24, 2002

(54) LYXOFURANOSYL BENZIMIDAZOLES AS ANTIVIRAL AGENTS

(75) Inventors: Leroy B. Townsend, Ann Arbor, MI (US); John C. Drach, Ann Arbor, MI (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/124,484

(22) Filed: Jul. 29, 1998

Related U.S. Application Data

(60) Provisional application No. 60/054,286, filed on Jul. 30, 1997, and provisional application No. 60/092,929, filed on Jul. 15, 1998.

(51) Int. Cl.[7] .................. A61K 31/70; C07H 19/052
(52) U.S. Cl. ........................... 514/43; 536/28.9
(58) Field of Search ............... 514/43; 536/28.9

(56) References Cited

U.S. PATENT DOCUMENTS 3,555,040 A    1/1971   Frick et al. .............. 548/304.4

(List continued on next page.)

FOREIGN PATENT DOCUMENTS

EP    0304 624 A2    7/1988

(List continued on next page.)

OTHER PUBLICATIONS

Ahmed, R. and Stevens, J.G., "Viral Persistence" in: Fundamental Virology, 2nd Ed., Fields et al. (Eds.), Raven Press, New York, pp. 241–265 (1991).

(List continued on next page.)

*Primary Examiner*—Johann Richter
*Assistant Examiner*—Lawrence Crane
(74) *Attorney, Agent, or Firm*—Birch, Stewart, Kolasch & Birch, LLP

(57) ABSTRACT

The present invention pertains to D- and L-lyxofuranosyl benzimidazole compounds. In one embodiment, the present invention pertains to D- and L-lyxofuranosyl benzimidazole compounds selected from the group consisting of compounds having a formula selected from the following:

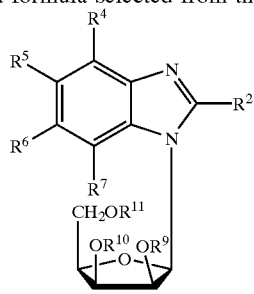

(beta-D)

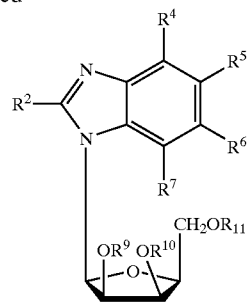

(beta-L)

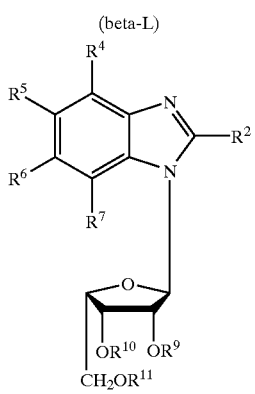

(alpha-L)

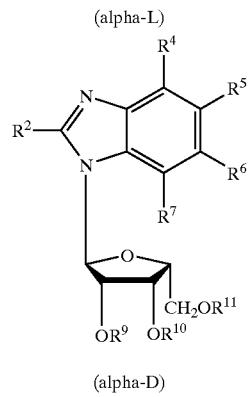

(alpha-D)

wherein $R^2$, $R^4$, $R^5$, $R^6$, and $R^7$ are independently the same or different and independently selected from the group consisting of: —H, —F, —Cl, —Br, —I, —$NO_2$, —$N(R^8)_2$, —$OR^8$, —$SR^{12}$, and —$CF_3$, wherein $R^8$ is independently —H or an alkyl group having 1–6 carbon atoms and wherein $R^{12}$ is independently —H or a hydrocarbyl group having 1–10 carbon atoms; and, $R^9$, $R^{10}$ and $R^{11}$ are independently the same or different and are H or a hydroxyl protecting group; anomeric and optical isomers thereof; and, pharmaceutically acceptable salts and prodrug derivatives thereof. The present invention also pertains to antiviral compositions using these compounds, methods of treating a viral infection using these compounds, and the use of these compounds in the preparation of a medicament for use in the treatment of a viral infection.

66 Claims, No Drawings

U.S. PATENT DOCUMENTS

| | | | |
|---|---|---|---|
| 3,655,901 A | 4/1972 | Jensen et al. | 548/307.4 |
| 3,839,575 A | 10/1974 | Gauss et al. | 514/394 |
| 4,680,176 A | 7/1987 | Berns et al. | 424/89 |
| 4,709,011 A | 11/1987 | Cohen et al. | 530/324 |
| 5,248,672 A | 9/1993 | Townsend et al. | 514/43 |
| 5,360,795 A | 11/1994 | Townsend et al. | 514/43 |
| 5,399,580 A | 3/1995 | Daluge | 514/394 |
| 5,534,535 A | 7/1996 | Townsend et al. | 514/394 |
| 5,574,058 A | 11/1996 | Townsend et al. | 514/394 |
| 5,646,125 A | 7/1997 | Townsend et al. | 514/43 |
| 5,654,283 A | 8/1997 | Townsend et al. | 514/43 |
| 5,665,709 A | 9/1997 | Townsend et al. | 514/43 |
| 5,679,342 A | 10/1997 | Houghton et al. | 424/93.21 |
| 5,705,490 A | 1/1998 | Townsend et al. | 514/43 |
| 5,712,255 A | 1/1998 | Townsend et al. | 514/43 |
| 5,840,743 A | 11/1998 | Townsend et al. | 514/395 |
| 5,874,413 A | 2/1999 | Townsend et al. | 514/43 |

FOREIGN PATENT DOCUMENTS

| | | |
|---|---|---|
| EP | 0521 463 A2 | 6/1992 |
| EP | 0350 467 B1 | 12/1993 |
| EP | 0 515 156 B1 | 2/1996 |
| FR | 1476350 | 4/1967 |
| FR | 1491244 | 8/1967 |
| WO | WO 92/07867 | 5/1992 |
| WO | WO93/18009 | 9/1993 |
| WO | WO 94/08456 | 4/1994 |
| WO | WO 95/23151 | 8/1995 |
| WO | WO96/01833 | 1/1996 |
| WO | WO96/07646 | 3/1996 |
| WO | WO 97/07125 | 2/1997 |
| WO | WO97/25316 | 7/1997 |
| WO | WO97/25337 | 7/1997 |
| WO | WO 97/27204 | 7/1997 |
| WO | WO 97/27205 | 7/1997 |
| WO | WO 98/35977 | 8/1998 |
| WO | WO 98/56761 | 12/1998 |
| WO | WO99/51619 | 10/1999 |

OTHER PUBLICATIONS

Alford, C.A. and Britt, W.J., "Cytomegalovirus" in: The Human Herpesviruses, Roizman et al. (Eds.), Raven Press, New York, pp. 227–255 (1993).

Alford, C.A. et al. "Congenital and Perinatal Cytomegalovirus Infections" Rev. Infect. Dis. 12:S745–S753 (1990). (Supplement #7, Sep./Oct., 1990).

Baker, B.R. et al., "Puromycin. Synthetic Studies. V. 6–Dimethylamino–9–(2'-acetaminoβ–D–glucopyranosyl)purine" J. Org. Chem. 19:1786–1792 (1954).

Bucknall, R.A., "The Effects of Substituted Benzimidazoles on the Growth of Viruses and the Nucleic Acid Metabolism of Host Cells" J. Gen. Virol. 1:89–99 (1967).

Chrisp, P. and Clissold, S.P., "Foscarnet. A Review of its Antiviral Activity, Pharmacokinetic Properties and Therapeutic Use in Immunocompromised Patients with Cytomegalovirus Retinitis" Drugs 41:104–129 (1991) (Issue No. 1).

Crumpacker, C.S., "Ganciclovir" New England J. Med. 335(10):721–729 (1996).(Sep. 5, '96).

Devivar, R.V. et al., "Benzimidazole Ribonucleosides: Design, Synthesis, and Antiviral Activity of Certain 2–(Alkylthio)– and 2–(Benzylthio)–5, 6–dichloro–β–D–ribofuranosyl)benzimidazoles" J. Med. Chem. 37:2942–2949 (1994). (Issue No. 18).

Field, A.K. and Biron, K.K., "'The End of Innocence' Revisited: Resistance of Herpesviruses to Antiviral Drugs" Clin. Microbiol. Rev. 7(1):1–13 (1994). (Jan. 1994).

Gallant, J.E. et al., "Incidence and Natural History of Cytomegalovirus Disease in Patients with Advanced Immunodeficiency Virus Disease Treated with Zidovudine" J. Infect. Dis. 166:1223–1227 (1992). (Dec. 1992).

Gibbs, E.P.J. and Rweyemamu, M.M., "Bovine herpesviruses. Part I: Bovine herpesvirus 1" Vet. Bull. 47:317–343 (1977). (Issue No. 5, May, 1977).

Gosselin, G. et al., "Synthesis and biological evaluation of new 5,6–dichlorobenzamidazole nucleoside derivatives" Antiviral Chem. & Chemother. 5(4):243–256 (1994).

Harrison, D. and Ralph, J.T., "Nucleophilic Substitution Reactions of 2–Chlorobenzimidazoles. Part 1. Formation of Benzimidazolin–2–ones and 2–Alkoxybenzimidazoles" J. Chem. Soc., pp. 236–239 (1965).

Hitchcock, M.J.M. et al., "Cidofovir, a new agent with potent anti–herpesvirus activity" Antiviral Chem. & Chemother. 7:115–127 (1996).

Kam, B.L. et al., "A General Method of Synthesis and Isolation, and an N.M.R.–Spectroscopic Study, of Tetra–O–acetyl–D–aldopentofuranoses" Carbohydrate Res. 69:135–142 (1979).

Kawashima, E. et al., "2,5,6–Trichlorobenzimidazole" in: Nucleic Acid Chemistry, Part 4, Townsend et al. (Eds.), John Wiley and Sons, New York, pp. 24–26 (1991).

Kucera, L.S. et al., "Activity of Triciribine and Triciribine–5'–monophosphate Against Human Immunodeficiency Virus Types 1 and 2" AIDS Res. Human Retroviruses 9(4):307–314 (1993).

Lalezari, J.P. et al., "(S)–1–[3–Hydroxy–2–(Phosphonylmethoxy)propyl]cytosine (Cidofovir): Results of a Phase I/II Study of a Novel Antiviral Nucleotide Analogue" J. Infect. Dis. 171:788–796 (1995)(Apr.

Murphy, F.A. and Kingsbury, D.W., "Virus Taxonomy" in: Fundamental Virology, 2nd Ed., Fields et al. (Eds.), Raven Press, New York, pp. 9–36 (1991).

Prichard, M.N. and Shipman, C., "A Three Dimensional Model to Analyze Drug–Drug Interactions" Antiviral Res. 14:181–206 (1990).

Prichard, M.N. et al., "Three–Dimensional Analysis of the Synergistic Cytotoxicity of Ganciclovir and Zidovudine" Antimicrobial Agents Chemother. 35:1060–1065 (1991). (Jun. 1991).

Prichard, M.N. et al., "A Microtiter Virus Yield Reduction Assay for the Evaluation of Antiviral Compounds Against Human Cytomegalovirus and Herpes Simplex Virus" J. Virol. Methods 28:101–106 (1990).

Roizman, B., "Herpesviridae: A Brief Introduction" in: Fundamental Virology, 2nd Ed., Fields et al. (Eds.), Raven Press, New York, pp. 841–847 (1991).

Roizman, B. and Sears, A.E, "Herpes Simplex Viruses and Their Replication" in: Fundamental Virology, 2nd Ed., Fields et al. (Eds.), Raven Press, New York, pp. 849–895 (1991).

Rosemeyer, H. et al., "Assignment of Anomeric Configuration of D–Ribo–, Arabino–, 2'–Deoxyribo–, and 2', 3'–Dideoxyribonucleosides by NOE Difference Spectroscopy" Nuecleosides & Nucleotides 8(4):587–597 (1989).

Shipman, C., Jr., "Evaluation of 4–(2–Hydroxyethyl)–1–piperazineëthane–Sulfonic Acid (HEPES) as a Tissue Culture Buffer" Proc. Soc. Exp. Biol. 130:305–310 (1969).

Shipman, C., Jr. et al., "Antiviral Activity of Arabinosyladenine and Arabinosylhypoxanthine in Herpes Simplex Virus–Infected KB Cells: Selective Inhibition of Viral DNA Synthesis in Synchronized Suspension Cultures" *Antimicrobial Agents Chemother.* 9(1):120–127 (1976). (Jan.,1976).

Stinski, M.F., "Cytomegalovirus and Its Replication" in: Fundamental Virology, 2nd Ed., Fields et al. (Eds.), Raven Press, New York, pp. 929–950 (1991).

Tamm, I. and Sehgal, P.B., "Halobenzimidazole Ribosides and RNA Synthesis of Cells and Viruses" *Adv. Virus Res.* 22:187–258 (1978).

Tamm, I. et al., "Inhibition of Influenza Virus Multiplication by N–Glycosides of Benzimidazoles" *J. Exp. Med.* 99:227–250 (1954).

Townsend, L.B. and Revankar, G.R., "Benzimidazole Nucleosides, Nucleotides, and Related Derivatives" *Chem. Reviews* 70:389–438 (1970). (Issue No. 3).

Townsend, L.B. et al., "Design, Synthesis, and Antiviral Activity of Certain 2,5,6–Trihalo–1–(β–D–ribofuranosyl)benzimidazoles" *J. Med. Chem.* 38:4098–4105 (1995). (Issue No. 20).

Turk, S.R. et al., "Pyrrolo[2,3–d]Pyrimidine Nucleosides as Inhibitors of Human Cytomegalovirus" *Antimicrobial Agents Chemother.* 31(4):544–550 (1987). (Apr., 1987).

Vorbrüggen, H. and Höfle, G., "On the Mechanism of Nucleoside Synthesis" *Chem. Ber.* 114:1256–1268 (1981).

Vorbrüggen, H. et al., "Nucleoside Synthesis with Trimethylsilyl Triflate and Perchlorate as Catalysts" *Chem. Ber.* 114:1234–1255 (1981).

Watson et al., in: Molecular Biology of the Gene, Fourth Edition, Benjamin/Cummings Publ. Co., Menlo Park, CA, pp. 904–905, 933, 935–936 (1987).

White, E.L. et al., "A TIBO Derivative, R82913, is a Potent Inhibitor of HIV–1 Reverse Transcriptase with Heteropolymer Templates" *Antiviral Res.* 16:257–266 (1991).

Zou, R. et al., "Synthesis and Antiviral Evaluation of Certain Disubstituted Benzimidazole Ribonucleosides" *J. Med. Chem.* 39:3477–3482 (1996). (Issue No. 18).

Zou, R. et al., "Design, Synthesis and Antiviral Evaluation of 2–Substituted 4,5–Dichloro– and 4,6–Dichloro–1–β–D–ribofuranosylbenzimidazoles as Potential Agents for Human Cytomegalovirus Infections" *J. Med. Chem.* 40:802–810 (1997). (Issue No. 5).

Zou, R. et al., "Design, Synthesis, and Antiviral Evaluation of 2–Chloro–5,6–dihalo–1–β–D–ribofuranosylbenzimidazoles as Potential Agents for Human Cytomegalovirus Infections" *J. Med. Chem.* 40:811–818 (1997). (Issue No. 5).

Koszalka, S. D. et al., "Benzimidazoles for the treatment of human cytomegalovirus" XII International Roundtable: *Nucleosides, Nucleotides and their Biological Applications*, La Jolla, CA (Abstract No. 85):A43 (Sep. 1996).

Pessler et al., "The HIV–1 Inducer of Short Transcripts Activates the Synthesis of 5,6–Dichloro– 1–β–D–(ribofuranosyl)benzimidazole–Resistant Short Transcripts In Vitro," *Journal of Biological Chemistry*, 273(9), 5375–5384 (Feb. 27, 1998).*

Kau et al., "Phosphorylation of the Core Protein of Hepatitis B Virus by a 46–Kilodalton Serine Kinase," *Journal of Virology*, 72(5), 3796–3803 (May, 1998).*

Underwood et al., "Inhibition of Human Cytomegalovirus DNA Maturation by a Benzimidazole Ribonucleoside Is Mediated Through the UL89 Gene Product," *Journal of Virology*, 72(1), 717–725 (Jan., 1998).*

Berkow et al., "The Merck Manual of Diagnosis and Therapy," Merck & Co., Rahway, NJ, 1992, only pp. 897–904 supplied (see "Hepatitis" and "Acute Viral Hepatitis.").*

* cited by examiner

LYXOFURANOSYL BENZIMIDAZOLES AS ANTIVIRAL AGENTS

RELATED APPLICATIONS

This application claims priority benefit under 35 U.S.C. §119(e) to U.S. Provisional Patent Application Serial No. 60/054,286 filed Jul. 30, 1997 and U.S. Provisional Patent Application Serial No. 60/092,929 filed Jul. 15, 1998, now abandoned.

TECHNICAL FIELD

This invention pertains to the general field of benzimidazole nucleoside analogs and their use as antiviral agents. More particularly, this invention pertains to benzimidazole nucleoside analogs wherein the sugar group is a lyxofuranosyl group and derivatives thereof. The present invention also pertains to methods of making such benzimidazole nucleoside analogs and derivatives, compositions comprising such compounds, the use of such compounds in antiviral treatment.

BACKGROUND

Throughout this application, various references including but not limited to publications, patents, and published patent applications are referred to by an identifying citation.

Members of the herpesvirus family (Herpesviridae) share a common virion architecture. A typical herpesvirion consists of (a) a core containing a linear, double-stranded DNA, (b) an icosahedral capsid, approximately 100–120 nm in diameter, containing 162 capsomeres, (c) an amorphous, sometimes asymmetric material that surrounds the capsid, designated as the tegument, and (d) an envelope containing viral glycoprotein spikes on its surface.

Major examples of human pathogens of the herpesviruses family include herpes simplex viruses (HSV) 1, 2, and cercopithecine herpesvirus 1 (B-virus); varicella-zoster (which causes chickenpox and shingles); Epstein-Barr virus (EBV, which causes mononucleosis); lymphocryptovirus; human herpesvirus 6 (HHV6); human herpesvirus 7 (HHV7) and kaposi-associated herpes virus (KHV); or human herpesvirus 8 (HHV8). Human cytomegalovirus (HCMV), also a human herpes virus, is a leading opportunistic pathogen among immunosuppressed individuals (see Alford, C. A.; Britt, W. J. Cytomegalovirus. In *The Human Herpesviruses*. Roizman, B.; Whitley, R. J.; Lopez, C. (Editors.) Raven Press, New York, 1993 pp. 227–255) and neonates (see Alford, C. A.; Stagno, S.; Pass, R. F.; Brit, W. J. Congenital and Perinatal Cytomegalovirus Infections in Bone Marrow Transplants. *Rev. Infect. Dis.* 1990, 12, s793–s804 and Gallant, J. E.; Moore, R. D.; Richman, D. D.; Keruly, J.; Chaisson, R. E. Incidence and Natural History of Cytomegalovirus Disease in Patients with Advanced Immunodeficiency Virus Disease Treated with Zidovudine. *J. Infect. Dis.* 1992, 166, 1223–1227).

Animal pathogens include infectious bovine rhinotracheitis virus, bovine mammillitis virus, cercopithecine herpesvirus 1 (B-virus), which are all simplexviruses; pseudorabies virus (PRV, of swine), equine rhinopneumonitis and coital exanthema viruses (varicellaviruses); baboon herpesvirus, pongine (chimpanzee) herpesvirus (lymphocryptovirus); Marek's disease virus (of fowl), turkey herpesvirus; herpesvirus ateles and herpesvirus saimiri (rhadinovirus); among others. For reviews see, Murphy et al., Virus Taxonomy, in Fields et al. (eds.) *Fundamental Virology*, 1991, Raven Press, New York, p. 9–36; Watson et al., *Molecular Biology of the Gene*, Fourth Edition, 1987, Benjamin/Cummings Publ. Co., Menlo Park, Calif., p. 904, 933.

Herpesvirus genomes, which are generally 120 to 230 kb long, encode 50 to 200 different proteins. These include a large array of enzymes involved in nucleic acid metabolism (e.g., thymidine kinase, thymidylate synthetase, dUTPase, ribonucleotide reductase, etc.), and DNA synthesis (e.g., DNA polymerase, helicase, primase).

In herpesviruses, the linear genome is characterized by repeated sequences, which vary in number, length and arrangement between the various classes of herpesvirus. In Epstein-Barr virus, for example, the ends of the genome have a large number of short (500-base pair) repetitions of the identical sequence as well as an internal sequence consisting of half a dozen repeats of a 3-kb sequence. In herpes simplex virus 1 and 2 and HCMV, portions of sequences from both termini are repeated in an inverted orientation and juxtaposed internally, dividing the genomes into two components, each of which consists of unique sequences flanked by inverted repeats. In this instance, both components (a long, L, arm and a short, S, arm) can invert relative to each other. DNA extracted from virions or infected cells consists of four equimolar populations differing in the relative orientation of the two components. For reviews see, Watson et al., 1987, p. 935; Roizman, Herpesviridae: A Brief Introduction, in Fields et al. (eds.) *Fundamental Virology*, 1991, Raven Press, New York, p. 841–847; Roizman et al., Herpes Simplex Viruses and Their Replication, in Fields et al. (eds.) *Fundamental Virology*, 1991, Raven Press, New York, p. 849–895.

To initiate infection, the virus attaches to receptors on a host cell. Fusion of the viral envelope with the plasma membrane rapidly follows initial attachment. The de-enveloped capsid is then transported to the nuclear pores, where DNA is released into the nucleus and rapidly circularizes. In the next steps, the transcription and translation of the herpes genes are tightly regulated. Three classes of genes are known, called $\alpha$, $\beta$ and $\gamma$ (or immediate early, early and late). Expression of the $\alpha$ genes is required to induce $\beta$ gene expression; expression of $\beta$ genes both induces $\gamma$ genes and shuts off $\alpha$ genes; and expression of $\gamma$ genes turns off $\beta$ genes. Thus, there are three distinct waves of herpesvirus gene expression during replication. Interestingly, the process seems to be circular in that at least one virion protein (a $\gamma$ gene product) is required to induce a gene expression soon after infection. This product enters with the virion and so helps to start the cycle. For reviews see, Watson et al., 1987, p. 935–936; Roizman et al., Herpes Simplex Viruses and Their Replication, in Fields et al. (eds.) *Fundamental Virology*, 1991, Raven Press, New York, p. 849–895.

Some herpesviruses such as HSV-1 and HSV-2 have a wide host-cell range, multiply efficiently and rapidly destroy infected cells. Others (e.g. EBV, HHV6) have a narrow host-cell range or, in the case of HCMV, replicate slowly. For reviews see, Roizman et al., Herpes Simplex Viruses and Their Replication, in Fields et al. (eds.) *Fundamental Virology*, 1991, Raven Press, New York, p. 849–895.

Herpesviruses replicate in the cell nucleus, wherein the nucleolus is displaced, disaggregated and then fragmented, and host chromosomes are marginated, which may lead to chromosome breakage. Host protein synthesis declines very rapidly (for most herpesviruses but not HCMV), host ribosomal RNA synthesis is reduced, and glycosylation of host proteins ceases. Production of progeny is invariably accompanied by the irreversible destruction of the infected cell. For reviews see, Roizman et al., Herpes Simplex Viruses and Their Replication, in Fields et al. (eds.) *Fundamental Virology*, 1991, Raven Press, New York, p. 849–895.

A variety of disease symptoms and a complex clinical course are caused by herpesviruses. In the case of a first infection in an adult human, the symptoms may be very severe. Herpesviruses can cause recurrent infections, and the disability associated with these recurrences is a significant health problem. The most frequent manifestations of recurrent herpetic disease states were disclosed to involve the orofacial and genital regions and recurrent herpetic keratitis was characterized as a leading cause of blindness in the United States. Herpetic genital infections with a high incidence of subsequent recurrent episodes were noted as being recognized more frequently and being associated with significant morbidity. Cohen et al., U.S. Pat. No. 4,709,011, issued Nov. 24, 1987.

In studies on the molecular basis of disease induced by HSV, the endpoint of the research objective—the disease— may be synonymous with the destruction of the central nervous system (CNS). To disseminate to a target organ, however, the virus may first multiply at peripheral sites. In experimental systems, neurovirulence, the model of the disease producing the phenotype of HSV, is the consequence of (i) peripheral multiplication; (ii) invasion of the CNS; (iii) growth in the CNS. Virulence loci have been ascribed to several sites in the HSV genome, but particularly in or around the domain of the tk gene and at one end of the L portion. However, nearly any mutation or deletion in the HSV genome results in decreased virulence. For reviews see, Roizman et al., Herpes Simplex Viruses and Their Replication, in Fields et al. (eds.) *Fundamental Virology*, 1991, Raven Press, New York, p. 849–895.

In the case of EBV and HCMV, acute hepatitis is frequently associated with infectious mononucleosis. Mononuclear cells are the major candidate as cells involved in the latent state of HCMV infection, and infectious mononucleosis may follow blood transfusions from seropositive to seronegative individuals. Seronegative individuals may also become infected via transplantation of cells or organs from seropositive donors. For reviews see, Ahmed et al., Viral Persistence, in Fields et al. (eds.) *Fundamental Virology*, 1991, Raven Press, New York, p. 241–265; Stinski, Cytomegalovirus and Its Replication, in Fields et al. (eds.) *Fundamental Virology*, 1991, Raven Press, New York, p. 929–950.

A herpesvirus of economic importance in the cattle industry is Bovine Herpesvirus-1 (BHV-1), which has been associated with a variety of clinical disease manifestations, including rhinotracheitis, vulvovaginitis, abortions, conjunctivitis, encephalitis and generalized systemic infections. Gibbs et al., 1977, Bovine herpesviruses. I: Bovine herpesvirus-1. *Vet. Bull.* (London) 47: 317–343.

The herpesvirus Pseudorabies virus (PRV), also called Aujeszky's disease virus (ADV), is a disease of all domestic animals, with the exception of the horse, and causes severe damage, especially among pigs and cattle. The pig is the natural host of ADV. Animals are infected via the nasal route and, after a primary virus multiplication in the mucous membranes of upper respiratory and digestive tracts, the virus spreads via nerves to the brain. The infection proceeds acutely to sub-clinically, which is mainly dependent on the virulence of the virus and the age of the pigs. PRV, just as other herpesviruses induces latent infections, namely in the nerve tissues. Berns et al., U.S. Pat. No. 4,680,176, issued Jul. 14, 1987.

Currently, only three drugs have been FDA-approved for the treatment of HCMV infections: gancyclovir (see Crumpacker, C. S. Ganciclovir. *New England J. Med.* 1996, 335, 721–729), foscarnet (see Chrisp, P.; Clissold, S. P. Foscarnet. A Review of its Antiviral Activity, Pharmacokinetic Properties and Therapeutic Use in Immunocompromised Patients with Cytomegalovirus Retinitis. *Drugs* 1991, 41, 104–129), and cidofivir (see Hitchcock, M. J.; Jaffe, H. S.; Martin, J. C.; Stagg, R. J. Cidofovir, a new agent with potent anti-herpesvirus activity. *Antiviral Chem. & Chemother.* 1996; 7: 115–127. (b) Lalezari, J. P.; Drew, W. L.; Glutzer, E.; James, C.; Miner, D.; Flaherty, J.; Fisher, P. E.; Cundy, K.; Hannigan, J.; Martin, J. C.; Jaffe, H. S. (S)-1-[3-Hydroxy-2-(phosphonylmethoxy)propyl]cytosine (Cidofovir): Results of a Phase I/II Study of a Novel Antiviral Nucleotide Analogue. *J. Infect. Dis.* 1995, 171, 788–796.). All of these drugs can lead to side-effects such as renal dysfunction (foscarnet and cidofivir) and granulocytopenia (ganciclovir). Additionally, potential drug resistance and poor oral bioavailability create a need for more potent and selective drugs (see Field, A. K.; Biron, K. K. "The End of Innocence" Revisited: Resistance of Herpesviruses to Antiviral Drugs. *Clin. Microbiol. Rev.* 1994, 7, 1–13).

Recent searches by the inventors for new antiviral drugs against herpes virus have focused on halogenated benzimidazole nucleoside analogs. The first reported (see. Tamm, I.; Folkers, K.; Shunk, C. H.; Horsfall, F. L., Jr. Inhibition of Influenza Virus Multiplication by N-Glycosides of Benzimidazoles. *J. Exp. Med.* 1954, 99, 227–250) synthesis and antiviral evaluations of this class of compounds, in 1954, reported 5,6-dichloro-1-(β-D-ribofuranosyl)benzimidazole (DRB) as the most active antiviral compound in their series. Unfortunately, DRB was subsequently found to affect multiple cellular processes and therefore, the activity was poorly separated from its cytotoxicity (see Bucknall, R. A. The Effects of Substituted Benzimidazoles on the Growth of Viruses and the Nucleic Acid Metabolism of Host Cells. *J. Gen. Virol.* 1967, 1, 89–99. (b) Tamm, I.; Sehgal, P. B. Halobenzimidazole Ribosides and RNA Synthesis of Cells and Viruses. *Adv. Virus Res.* 1978; 22:187–258).

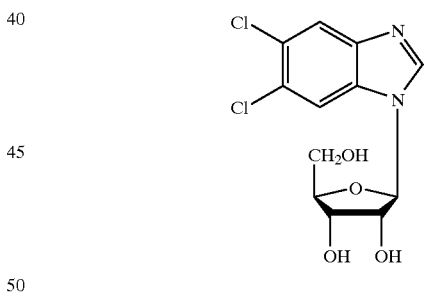

"DRB"
1-(beta-D-ribofuranosyl)-
5,6-dichloro-benzimidazole

Subsequently, the synthesis of several DRB analogs modified on the heterocyclic ring has been reported (see Townsend, L. B.; Revankar, G. R. Benzimidazole Nucleosides, Nucleotides, and Related Derivatives. *Chem. Reviews* 1970; 70:389–438). Among these, the 2-substituted-5,6-dichloro-benzimidazole ribonucleosides were found to be the most potent (see Townsend, L. B.; Devivar, R. V.; Turk, S. T.; Nassiri, M. R.; Drach, J. C. Design, Synthesis, and Antiviral Activity of Certain 2,5,6-Trihalo-1-(β-D-ribofuranosyl)benzimidazoles. *Med. Chem.* 1995, 38, 4098–4105; Zou, R.; Ayres, K. R.; Drach, J. C.; Townsend, L. B. Synthesis and Antiviral Activity of Certain Disubstituted Benzimidazole Ribonucleosides. *J. Med. Chem.* 1996, 39, 3477–3482; Zou, R.; Drach, J. C.; Townsend, L. B. Design, Synthesis, and Antiviral Evaluation of 2-Chloro-5,6-dihalo-1-β-D-ribofuranosylbenzimidazoles as Potential Agents for Human Cytomegalovirus Infections. *J. Med. Chem.* 1997, 40, 811–818; and Zou, R.; Drach, J. C.; Townsend, L. B. Design, Synthesis and Antiviral Evaluation of 2-Substituted 4,5-Dichloro- and 4,6-Dichloro-1-β-D-ribofuranosylbenzimidazoles as Potential Agents for Human Cytomegalovirus Infections. *J. Med. Chem.* 1997, 40, 802–810). For example, 2,5,6-trichloro-1-(β-D-ribofuranosyl)benzimidazole (TCRB) and 2-bromo-5,6-dichloro-1-(β-D-ribofuranosyl)benzimidazole (BDCRB) were demonstrated to be significant inhibitors of HCMV and this activity was well separated from its cytotoxicity (see Townsend, L. B.; Devivar, R. V.; Turk, S. T.; Nassiri, M. R.; Drach, J. C. Design, Synthesis, and Antiviral Activity of Certain 2,5,6-Trihalo-1-(β-D-ribofuranosyl)benzimidazoles. *J. Med. Chem.* 1995, 38, 4098–4105).

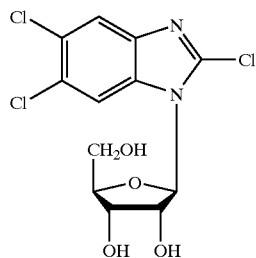

1-(beta-D-ribofuranosyl)-
2,5,6-trichloro-benzimidazole

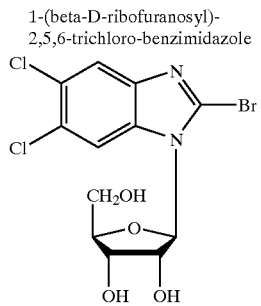

"BDCRB"

1-(beta-D-ribofuranosyl)-
2-bromo-5,6-dichloro-
benzimidazole

Additionally, several 2-alkylthio- and 2-benzylthio analogs have been prepared (see Devivar, R. V.; Kawashima, E.; Revankar, G. R.; Breitenbach, J. M.; Kreske, E. D.; Drach, J. C.; Townsend, L. B. Benzimidazole Ribonucleosides: Design, Synthesis, and Antiviral Activity of Certain 2-(Alkylthio)- and 2-(Benzylthio)-5,6-dichloro-β-D-ribofuranosyl)benzimidazoles. *J. Med. Chem.* 1994, 37, 2942–2948).

In addition to these D-carbohydrate derivatives, several carbocyclic (see Townsend, L. B.; Drach, J. C.; Good, S. S.; DaLuge, S. M.; Martin, M. C. Therapeutic Nucleosides. U.S. Pat. No. 5,534,535 issued Jul. 9, 1996) and L-carbohydrate (see Koszalka, G. W.; Chamberlain, S. D.; Daluge, S. M.; Boyd, F. L.; Tidwell, J. H.; Martin, M. T.; Harvey, R. J.; Frick, L. W.; Perkins, D. G.; Wang, L. H.; Drach, J. C.; Townsend, L. B.; Biron, K. K. Benzimidazoles for the treatment of human cytomegalovirus infection. In *XII International Roundtable: Nucleosides, Nucleotides and their Biological Applications*, La Jolla, Calif., September 1996) derivatives have been synthesized and evaluated.

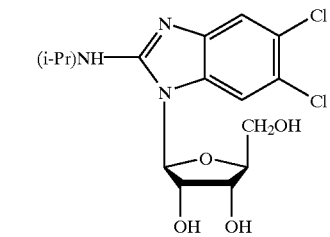

1-(beta-L-ribofuranosyl)-
2-isopropylamino-
5,6-dichloro-benzimidazole

The present invention pertains to a new class of benzimidazole nucleoside analogs wherein the sugar group is a lyxofuranosyl group or a derivative thereof.

SUMMARY OF THE INVENTION

One aspect of the present invention pertains to D- and L-lyxofuranosyl benzimidazole compounds. In one embodiment, the present invention pertains to D- and L-lyxofuranosyl benzimidazole compounds selected from the group consisting of compounds having a formula selected from the following:

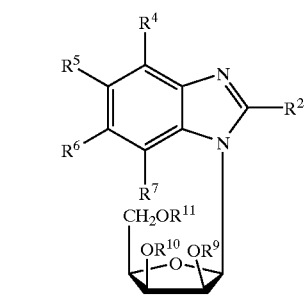

(beta-D)

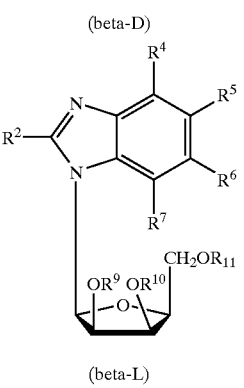

(beta-L)

-continued

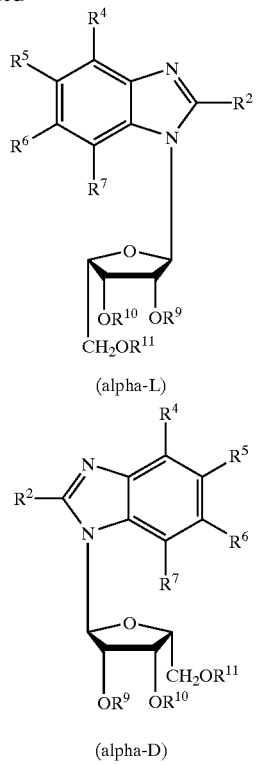

(alpha-L)

(alpha-D)

wherein $R^2$, $R^4$, $R^5$, $R^6$, and $R^7$ are independently the same or different and independently selected from the group consisting of: —H, —F, —Cl, —Br, —I, —$NO_2$, —$N(R^8)_2$, —$OR^8$, —$SR^{12}$, and —$CF_3$, wherein $R_8$ is independently —H or an alkyl group having 1–6 carbon atoms (including methyl, ethyl, propyl, isopropyl, and cyclopropyl) and wherein $R^{12}$ is independently —H or a hydrocarbyl group (including aliphatic, alicyclic, and aromatic groups, including alkyl, aryl, aralkyl, alkaryl groups) having 1–10 carbon atoms; $R^9$, $R^{10}$ and $R^{11}$ are independently the same or different and are H or a hydroxyl protecting group (such as acetyl); anomeric and optical isomers thereof; and, pharmaceutically acceptable salts and prodrug derivatives thereof.

In one embodiment, the present invention pertains to D- and L-lyxofuranosyl benzimidazole compounds wherein: $R^2$ is selected from the group consisting of: —H, —F, —Cl, —Br, —I, and —$N(R^8)_2$; $R^4$ and $R^7$ are both —H; $R^5$ and $R^6$ are independently the same or different and selected from the group consisting of: —H, —F, —Cl, —Br, and —I; anomeric and optical isomers thereof; chemically protected forms thereof; and, pharmaceutically acceptable salts and prodrug derivatives thereof.

In one embodiment, the present invention pertains to α-D-lyxofuranosyl benzimidazole compounds. In one embodiment, the present invention pertains to β-D-lyxofuranosyl benzimidazole compounds. In one embodiment, the present invention pertains to α-L-lyxofuranosyl benzimidazole compounds. In one embodiment, the present invention pertains to β-L-lyxofuranosyl benzimidazole compounds.

In one embodiment, the present invention pertains to D- and L-lyxofuranosyl benzimidazole compounds selected from the group consisting of:

1-(lyxofuranosyl)-2,5,6-trichloro-benzimidazole;
1-(lyxofuranosyl)-2-bromo-5,6-dichloro-benzimidazole;
1-(lyxofuranosyl)-2-methylamino-5,6-dichloro-benzimidazole;
1-(lyxofuranosyl)-2-isopropylamino-5,6-dichloro-benzimidazole;
1-(lyxofuranosyl)-2-cyclopropylamino-5,6-dichloro-benzimidazole;
1-(lyxofuranosyl)-2-thio-5,6-dichloro-benzimidazole;
1-(lyxofuranosyl)-2-benzylthio-5,6-dichloro-benzimidazole;
1-(lyxofuranosyl)-2-methylthio-5,6-dichloro-benzimidazole;

anomeric and optical isomers thereof;
chemically protected forms thereof; and,
pharmaceutically acceptable salts and prodrug derivatives thereof.

Compounds not encompassed by the present invention include 1-(5'-deoxy-lyxofuranosyl)-2,5,6-trichloro-benzimidazole, 1-(5'-deoxy-lyxofuranosyl)-2-bromo-5,6-dichloro-benzimidazole, and 1-(5'-deoxy-lyxofuranosyl)-2-isopropylamino-5,6-dichloro-benzimidazole.

Another aspect of the present invention pertains to compositions comprising a biologically acceptable carrier and a D- or L-lyxofuranosyl benzimidazole compound of the present invention. In one aspect, the carrier may be a pharmaceutically acceptable carrier as defined in the art.

Another aspect of the invention pertains to inhibiting viral replication and propagation by contacting the virus with a D- or L-lyxofuranosyl benzimidazole compound of the present invention.

Yet another aspect of the present invention pertains to methods for treating and/or preventing a viral infection comprising the step of administering to an infected host a therapeutically effective amount of an antiviral lyxofuranosyl benzimidazole compound of the present invention, alone or in combination with a carrier such as a pharmaceutically acceptable carrier.

A further embodiment of this invention pertains to methods for treating and/or preventing a hepatitis viral infection, e..g, hepatitis B and hepatitis C, comprising contacting the virus with an effective amount of an antiviral lyxofuranosyl benzimidazole compound of the present invention, alone or in combination with a carrier such as a pharmaceutically acceptable carrier..

Still another aspect of the present invention pertains to the use of a D- or L-lyxofuranosyl benzimidazole compound of the present invention in the preparation of a medicament for use in the treatment of a viral infection.

Yet another aspect of the present invention pertains to methods of preparing the D- or L-lyxofuranosyl benzimidazole compounds of the present invention.

As will become apparent, preferred features and characteristics of one aspect of the invention are applicable to any other aspect of the invention.

DETAILED DESCRIPTION OF THE INVENTION

A. The Antiviral Compounds of the Present Invention

Generally, the antiviral compounds of the present invention are benzimidazole nucleoside analogs which comprise a benzimidazole group attached via the 1-position to a sugar group, Q.

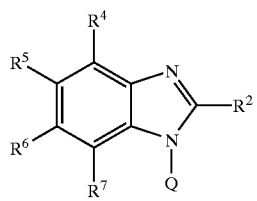

The term "sugar group," as used herein, pertains to sugar groups in their cyclic form, for example, those derived from furanose (5-membered ring). Examples of sugar groups include threofuranosyl (from threose, a four-carbon sugar); ribofuranosyl (from ribose, a five-carbon sugar); arafuranosyl (also often referred to as arabinofuranosyl; from arabinose, a five-carbon sugar); xylofuranosyl (from xylose, a five-carbon sugar), and lyxofuranosyl (from lyxose, a five-carbon sugar). Examples of these sugars are illustrated below.

beta-D-threo-furanosyl:

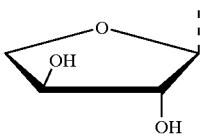

beta-D-ribo-furanosyl:

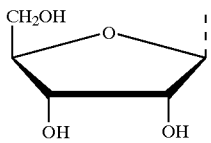

beta-D-arabino-furanosyl:

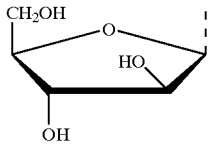

beta-D-xylo-furanosyl:

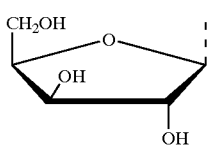

beta-D-lyxo-furanosyl:

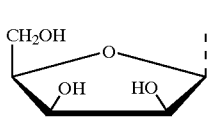

More specifically, the compounds of the present invention comprise a benzimidazole group which is attached via the 1-position to a lyxofuranosyl group (or a derivative thereof) via the 1'-position. Lyxofuranosyl is characterized by the 2'-OH, 3'-OH and 4'-CH$_2$OH being on the same side of the furanosyl plane. In this way, lyxofuranosyls and ribofuranosyl are often referred to as 4'-epimers, since pairs differ by the configuration at the 4'-carbon.

The term "benzimidazole group," as used herein, pertains to benzimidazol-1-yl groups which may be independently substituted at one or more of the 2-, 4-, 5-, 6-, 7-positions with substituents $R^2$, $R^4$, $R^5$, $R^6$, and $R^7$, respectively, as illustrated below.

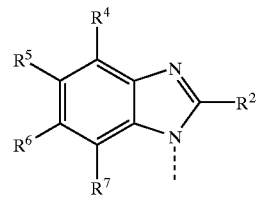

Examples of benzimidazole substituents, $R^2$, $R^4$, $R^5$, $R^6$ and $R^7$, include —H, halogens (e.g., —F, —Cl, —Br, —I), —NO$_2$, —NR$_2$ (where R is independently —H or an alkyl group having 1–6 carbon atoms), —OR (where R is —H or an alkyl group having 1–6 carbon atoms), —SR (where R is —H or a hydrocarbyl group having 1–10 carbon atoms), and —CF$_3$.

Examples of benzimidazole groups include halobenzimidazoles, such as halo-, dihalo-, trihalo-, tetrahalo-, and pentahalobenzimidazoles, including but not limited to, 2,5,6-trihalobenzimidazole (e.g., 2,5,6-trichlorobenzimidazole, 2-bromo-5,6-dichlorobenzimidazole), 2,4,6-trihalobenzimidazole (e.g., 2,4,6-trichlorobenzimidazole, 2-bromo-4,6-dichlorobenzimidazole), 2,4,5,6-tetrahalobenzimidazole (e.g., 2,4,5,6-tetrachlorobenzimidazole, 2-bromo4,5,6-trichlorobenzimidazole). Other examples of benzimidazole groups include 2-substituted-4,5-dihalobenzimidazoles (e.g., 2-amino-4,5-dichlorobenzimidazole, 2-isopropylamino-4,5-dichlorobenzimidazole, 2-methoxy-4,5-dichlorobenzimidazole, 2-trifluoromethyl-4,5-dichlorobenzimidazole). A number of benzimidazoles compounds, and methods for their preparation, are known in the art. See, for example, U.S. Pat. Nos. 5,248,672 and 5,360,795.

In one embodiment of the present invention, the benzimidazole group is a 5,6-dichlorobenzimidazole group. In another embodiment of the present invention, the benzimidazole group is a 2,5,6-trichlorobenzimidazole group. In yet another embodiment, the benzimidazole group is a 2-substituted-5,6-dichlorobenzimidazole group, wherein the 2-substituent is an amino group (i.e., —NH$_2$), a substituted amino group (e.g., —NHR, —N(R)$_2$, wherein R is an alkyl group having 1–6 carbon atoms), a halo group (e.g., —F, —Cl, —Br, —I), a sulfhydryl group (i.e., —SH), or a thioether group (i.e., —SR, wherein R is a hydrocarbyl group having 1–10 carbon atoms).

Examples of the compounds of the present invention include those listed below, as well as anomeric (i.e., α- and β-) and optical (i.e., D- and L-) isomers thereof; and pharmaceutically acceptable salts and prodrug derivatives thereof.

1-(lyxofuranosyl)-2,5,6-trichloro-benzimidazole;
1-(lyxofuranosyl)-2-bromo-5,6-dichloro-benzimidazole;
1-(lyxofuranosyl)-2-methylamino-5,6-dichloro-benzimidazole;
1-(lyxofuranosyl)-2-isopropylamino-5,6-dichloro-benzimidazole;
1-(lyxofuranosyl)-2-cyclopropylamino-5,6-dichloro-benzimidazole;
1-(lyxofuranosyl)-2-thio-5,6-dichloro-benzimidazole;

1-(lyxofuranosyl)-2-benzylthio-5,6-dichloro-benzimidazole; and 1-(lyxofuranosyl)-2-methylthio-5,6-dichloro-benzimidazole.

The term "pharmaceutically acceptable salt or prodrug derivative," as used herein, related to any pharmaceutically acceptable salt, ester, ether, salt of an ester, solvate, such as ethanolate, or other derivative of a compound of the present invention which, upon administration to a recipient, is capable of providing (directly or indirectly) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system).

Salts of the compounds of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the compounds of the present invention include carboxylic acid esters (i.e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group. Examples of lyxofuranosyl prodrug derivatives of the present invention include, for example, those with chemically protected hydroxyl groups (e.g., with O-acetyl groups), such as 2'-O-acetyl-lyxofuranosyl; 3'-O-acetyl-lyxofuranosyl; 5'-O-acetyl-lyxofuranosyl; 2',3'-di-O-acetyl-lyxofuranosyl and 2',3',5'-tri-O-acetyl-lyxofuranosyl.

Ethers of the compounds of the present invention include methyl, ethyl, propyl, butyl, isobutyl, and sec-butyl ethers.

B. Methods of Using the Antiviral Compounds of the Present Invention

One aspect of the present invention pertains to methods for inhibiting viral replication and/or propagation in vitro, ex vivo or in vivo, by contacting the virus with an effective amount of a compound effective to inhibit viral replication and/or propagation. When the contacting is done in vitro, the compounds are useful to screen for other antiviral compounds that may be used independently or in combination with the compounds disclosed herein. The compounds also are useful for treating and/or preventing a viral infection by administering to an infected host a therapeutically effective amount of a lyxofuranosyl benzimidazole compound of the present invention. In one embodiment, such methods include administering to an infected host a composition of a pharmaceutically acceptable carrier and a therapeutically effective amount of an antiviral lyxofuranosyl benzimidazole compound of the present invention.

The term "therapeutically effective amount" is to include a prophylactically effective amount and refers to an amount effective in treating or preventing a viral infection in a patient either as monotherapy or in combination with other agents. The term "treating" as used herein refers to the alleviation of symptoms of a particular disorder in a patient or the improvement of an ascertainable measurement associated with a particular disorder or a reduction in viral titer in the host. One of skill in the art can determine when a host has been "treated" by noting a reduction in viral load or an alleviation in symptoms associated with viral infection. The term "prophylactically effective amount" refers to an amount effective in preventing viral infection in a host. As used herein, the term "host" refers to a mammal, such as a mouse, bovine, rat or a human patient.

The term "biologically acceptable carrier" refers to a carrier or adjuvant that may be administered to a host or patient, together with a compound of this invention, and which does not destroy the pharmacological activity thereof and is nontoxic when administered in doses sufficient to deliver an effective amount of the antiviral compound. Examples of suitable carriers include liquid phase carriers, such as sterile or aqueous solutions, as well as those described below.

As shown below, the compounds of this invention are potent antiviral drugs, and are particularly effective against DNA virus, e.g., herpes-type viruses such as HCMV, HBV and HSV-1, and as such, when combined with carriers, provide compositions for inhibiting viral reproduction and proliferation in vitro, ex vivo or in vivo. However, it should be understood, although not explicitly stated, that other virus, such as HHV-6 and HIV can be inhibited by the compounds of this invention. Methods of determining efficacy against these viruses are provided below. In addition RNA virus can be inhibited by the compounds of this invention.

The compounds of this invention also can be employed in combination with other therapeutic agents for the inhibition of the replication or propagation of the above virus and associated conditions. Combination therapies according to the present invention comprise the administration of at least one compound of the present invention and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent (s) and the relative timings of administration will be selected in order to achieve the desired combined therapeutic effect. Preferably the combination therapy involves the administration of one compound according to the invention and one of the agents mentioned herein below. The term "operative combination" is intended to include any chemically compatible combination of a compound of the present invention with other compounds of the present invention or other compounds outside the present invention (such as ganciclovir, AZT, and foscarnet), as long as the combination does not eliminate the antiviral activity of the compound of the present invention.

Examples of other active ingredients include agents that are effective for the treatment of viral infections or associated conditions are (1-alpha, 2-beta, 3-alpha)-9-[2,3-bis (hydroxymethyl)cyclobutyl]guanine [(−)BHCG, SQ-34514], oxetanocin-G(3,4-bis-(hydroxymethyl)-2-oxetanosyl]guanine), acyclic nucleosides (e.g., acyclovir, valaciclovir, famciclovir, ganciclovir, penciclovir), acyclic nucleoside phosphonates (e.g., (S)-I-(3-hydroxy-2-phosphonylmethoxypropyl)cytosine (HPMPC), ribonucleotide reductase inhibitors such as 2-acetylpyridine 5-[(2-chloroanilino)thiocarbonyl] thiocarbonohydrazone, 3'-azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as ritonovir, indinavir, 141W94, nelfinavir, sanquinavir, and 3S-[3R* (1 S*,2R*)]-[3-[[(4-aminophenyl) sulphonyl](2-methylpropyl)-amino]-2hydroxy-I-phenylmethyl)propyl]carbamic acid, tetrahydro-3-furanyl ester (141W94), oxathiolane nucleoside analogues such as (−)-cis-1-(2-hydroxymethyl)-1,3-oxathiolane 5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6(cyclopropylamino)-9H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)- 3H-1,4-benzodiazepin-2-(H)one (Ro5-3335), 7-chloro-1,3-dihydro-5-(1H-pyrrol-2-yl)-3H-1,4-benzodiazepin-2-amine (Ro24-7429), interferons such as (α-interferon, renal excretion inhibitors such as probenecid, nucleoside transport inhibitors such as dipyridamole; pentoxifylline, N-acetylcysteine (NAC), Procysteine, (α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or non-nucleoside reverse transcriptase inhibitors such as nevirapine (BI-RG-587), loviride (α-APA) and delavuridine (BHAP), and phosphonoformic acid.

The compounds of the invention could also be used to treat HCMV and HSV-1 infections in AIDS patients already receiving the antiviral drug zidovudine (AZT) and/or 3TC. Combination therapies with AZT may provide the advantage of less toxicity over the combination of ganciclovir with AZT. The combination of the compounds of this invention with AZT may produce less cytotoxicity (i.e. antagonism) in cultured human cells than either agent used alone. In contrast, combination of ganciclovir with AZT may produce greater cytotoxicity in human cells than the use of either of these drugs alone.

This invention also provides a method of reducing or inhibiting viral reproduction and proliferation in a virally infected cell or population of cells by contacting the cell or population with an effective amount of a compound of this invention and under suitable conditions, such that viral reproduction and proliferation is inhibited. One of skill in the art can easily determine when viral reproduction and proliferation has been reduced or inhibited by noting a reduction in viral titer or an increase of survival of the infected cells as compared to untreated, infected cells. Methods of assaying viral titer are well known to those of skill in the art and are exemplified below. It should be readily understood that by inhibiting and reducing viral replication and proliferation, viral infectivity also is inhibited and reduced and the cells are suitably treated for viral infection. Associated pathologies also are treated. In one embodiment, herpes-type virus such as HCMV, hepatitis virus, e.g., hepatitis B virus (HBV), or HSV-1 infection are treated or prevented.

For the purposes of this invention, a "cell" is intended to include, but not be limited to a mammalian cell, e.g., a mouse cell, a bovine cell, a rat cell, a woodchuck cell, a simian cell, or a human cell. Viruses which are effectively treated by the compounds, compositions and methods of this invention include DNA and RNA viruses, particularly herpes-type viruses. Examples of herpes-type viruses, or herpesviridae, are herpes simplex virus 1 (HSV-1), herpes simplex virus 2 (HSV-2), varicella-zoster virus (VZV), Epstein-Barr virus (EBV), human cytomegalovirus (HCMV), human herpes virus 6 (HHV-6), human herpes virus 7 (HHV-7), and human herpes virus 8 (HHV-8). The compounds of the present invention are particularly useful in the treatment of HCMV and HSV-1 infections, and associated pathologies such as restenosis. They also are suitably used in the treatment of hepatitis associated disorders such as hepatocellular carcinoma (See, U.S. Pat. No. 5,679,342).

Effective amounts are easily determined by those of skill in the art and will vary with the cell, virus being effected and the purpose of the treatment. For example, when utilizing the drug in cell culture, it is important that the amount of drug not be cytotoxic to the cells.

"Suitable conditions" include in vitro, ex vivo or in vivo. When the method is practiced in vitro, contacting may be effected by incubating the cells with an effective antiviral amount of the compound, effective to inhibit viral reproduction and proliferation in the cell or culture of cells. The compound can be added directly to the culture media or combined with a carrier prior to addition to the cells. In vitro, the method is particularly useful for inhibiting viral reproduction, proliferation and therefore infection in laboratory cell cultures. Ex vivo, the compounds are useful to inhibit viral reproduction and proliferation in blood and plasma prior to reintroduction into a patient.

The use of the compounds and methods in vitro also provides a powerful bioassay to screen for novel drugs or compounds which provide similar or enhanced antiviral activity. Using the methods set forth below, the drug to be tested is assayed under the same conditions as a compound of this invention. Antiviral and cytotoxicity of the test drug can then be compared to a compound of this inventive group.

Although the compounds are shown below to be particularly effective against HCMV and HSV-1, it is within the scope of this invention that other viruses are effectively treated with the compounds of this invention by use of methods described herein and others well known to those of skill in the art. Other viruses that can be treated as defined herein and within the scope of the present invention include all members of the herpes family, and human immunodeficiency virus (HIV) and hepatitis viruses, for example, hepatitis B virus (HBV). Methods of determining the efficacy of any of the compounds of this invention against HBV are well known in the art; see for example, the methods shown in U.S. Pat. No. 5,399,580 to Daluge.

An additional member of the hepatitis virus family that can be treated as defined herein is hepatitis C virus (HCV). U.S. Pat. No. 5,679,342, issued to Houghton et al. describes in detail methods for employing an extracorporeal cell system infected with HCV to screen for the compounds most active against HCV. In brief, the method comprises: (a) providing a composition containing the compound of this invention to be tested; (b) providing an extracorporeal cell system capable of being infected by HCV; (c) providing a biological sample containing infective HCV; (d) incubating the compositions of (a) and (c) with the cell system of (b) under conditions that would, in the absence of (a), allow infection of HCV in the cell system; and (e) detecting inhibition of viral infection after incubation. Preferred cell systems as disclosed in U.S. Pat. No. 5,679,342, include hepatocytes, macrophages, more preferably Kupffer macrophages, and B lymphocytes. Cell lines derived from organs of hepatocytic origin also are suitable for use in the assay described above. One can also use the above noted assay to test for the inhibition of viral replication by incubating the compositions of (a) and (b) under conditions that would, in the absence of (a), allow replication of HCV in the cell line and then detecting inhibition of viral replication after incubation.

Another method well known in the art for testing the antiviral activity of compounds against HCV is the helicase inhibition assay described, for example, in Lain et al., (1991) *Nucleic Acids Res.* 69:1720–1726 and Kim et al., (1995) *Biochem. Biophys,* Res. Comm. 160–166.

When the method is practiced in vivo in a subject such as a human patient, the compound can be added to a pharmaceutically acceptable carrier and systemically or topically administered to the subject, such as a human patient or a mammal such as a mouse, a rat, a woodchuck, or a simian.

The compositions also can be administered to subjects or individuals susceptible to or at risk of a viral infection, such as HCMV, HSV-1 or herpes virus infection. Thus, this invention also provides a prophylactic method of inhibiting viral replication, proliferation and/or viral infection in a subject by administering to a subject a prophylactically effective amount of the compound or composition under suitable conditions such that viral replication, proliferation or infection is inhibited. A "prophylactically effective amount" is an amount which inhibits viral infection, reproduction and proliferation in a subject challenged with the virus without toxicity to the cells and subject being treated.

It should be understood that by preventing or inhibiting viral proliferation, infection and replication in a subject or individual, the compositions and methods of this invention also provide methods for treating, preventing or ameliorating the symptoms or disorders associated with the viral infection, such as inclusion disease, blindness, mononucleosis, restenosis (HCMV); chickenpox, shingles (varicella-zoster virus); infectious mononucleosis, glandular, fever, and Burkittis lymphoma (Epstein-Barr virus); cold sores (herpes simplex virus 1); genital herpes (herpes simplex virus 2); roseola infantum (human herpes virus 6, human herpes virus 7); kaposi sarcoma (human herpes virus 8). Thus, this invention also provides methods of ameliorating, preventing, or treating disorders or symptoms associated with viral infection, e.g., HCMV, HSV-1 and herpes viral infection, e.g., restenosis, opportunistic infections (such as retinal infections, gastrointestinal infections, pneumonia, CNS infections or liver damage) and in utero infections, by administering to the subject an effective amount of a compound of this invention under suitable conditions such that the disorder or symptom is ameliorated, prevented, or treated.

Restenosis is the narrowing of the blood vessels which can occur after injury to the vessel wall, for example injury caused by balloon angioplasty or other surgical techniques, and is characterized by excessive proliferation of smooth muscle cells in the walls of the blood vessel treated. Restenosis following angioplasty (RFA) occurs in patients who have been treated for coronary artery disease by balloon angioplasty. It is thought that in many patients suffering from RFA, viral infection, particularly by CMV and/or HHV-6, of the patient plays a pivotal role in the proliferation of the smooth muscle cells in the coronary vessel treated.

Restenosis can occur following a number of surgical techniques, for example, transplant surgery, vein grafting, coronary by-pass grafting and, most commonly, following angioplasty.

Angioplasty is a surgical technique wherein atherosclerotic stenoses in the peripheral, renal and coronary vasculature are opened up by compressing and/or tearing the plaque on the vessel walls, typically by means of a pressurized balloon catheter. Unfortunately, in 25 to 50% of cases, particularly those involving the coronary vasculature, the treated vessel restenosis within a few months so that the operation must be repeated. Alternatives to the balloon catheter, such as pulsed lasers and rotary cutters, have been developed with a view to reducing or preventing restenosis following angioplasty, but have met with limited success. A number of drugs including anti-coagulants and vasodilators have also been tried with disappointing or equivocal results.

There is now a strong body of evidence, from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material. Thus, the compounds of this invention can be used in methods to prevent or treat restenosis in a susceptible subject or patient.

Administration in vivo can be effected in one dose, continuously or intermittently throughout the course of treatment. Methods of determining the most effective means and dosage of administration are well known to those of skill in the art and will vary with the composition used for therapy, the target virus, the purpose of the therapy, the target cell being treated, and the subject being treated. Single or multiple administrations can be carried out with the dose level and pattern being selected by the treating physician. Suitable dosage formulations and methods of administering the compounds can be found below.

The compounds of the present invention all exhibit antiviral activity against HCMV, herpes viral infection and HSV-1, many with acceptable cytotoxicity. It will be appreciated that compounds of the present invention which exhibit relatively high antiviral activity versus cytotoxicity, i.e. good selectivity, are preferred. It will also be appreciated that antiviral treatment in accordance with the present invention encompasses the treatment of viral infections, as well as prophylactic treatment which may be desired in certain situations, e.g. in immunocompromised patients, such as bone marrow and organ transplant patients as well as patients harboring HIV who are particularly susceptible to HCMV, herpes viral ,or HSV-1 infection.

The compounds and compositions of the present invention can be used in the manufacture of medicaments and in antiviral treatment of humans and other animals by administration in accordance with conventional procedures, such as an active ingredient in pharmaceutical compositions.

The pharmaceutical compositions can be administered topically, orally, intranasally, parenterally or by inhalation therapy, and may take the form of tablets, lozenges, granules, capsules, pills, ampoules, suppositories or aerosol form. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, the virus being treated and the nature of the infection.

In general, a suitable dose for each of the above-named viral infections, e.g., HCMV and HSV-1, is in the range of about 0.1 to about 250 mg per kilogram body weight of the recipient per day, preferably in the range of about 1 to about 100 mg per kilogram body weight per day and most preferably in the range of about 5 to about 20 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about $2\,\mu M$ to about $100\,\mu M$, preferably about $5\,\mu M$ to about $70\,\mu M$, most preferably about 1 to about $50\,\mu M$. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient. The use of operative combinations is contemplated to provide therapeutic combinations requiring a lower total dosage of each component antiviral agent than may be required when each individual therapeutic compound or drug is used alone, thereby reducing adverse effects, e.g., cytotoxicity.

While it is possible for the active ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For infections of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 100% w/w. When formulated in an ointment, the active ingredient may be employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulation in a concentration of about 0.5 to about 20%, advantageously about 0.5 to about 100% particularly about 1.5% w/w.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Compounds of the formula of the present invention may also be presented for the use in the form of veterinary formulations, which may be prepared, for example, by methods that are conventional in the art.

C. Methods for Preparing the Antiviral Compounds of the Present Invention

It has been shown that 2,3,5-tri-O-acetyl-glycofuranosyl nucleosides can be prepared by a modified Vorbrüggen procedure from 1,2,3,5-tetra-O-acetyl-glycosides (see Vorbruggen, H.; Krolikiewicz, K.; Bennua, B. Nucleoside Synthesis with Trimethylsilyl Triflate and Perchlorate as Catalyst. *Chem. Ber.* 1981, 114:1234–55). The anomeric configuration is predominately trans, with respect to the 1'-heterocyclic moiety and 2'-O-acetyl group, in most cases (see Baker, B. R.; Joseph, J. P.; Schaub, R. E.; Williams, J. H. Puromycin Synthetic Studies. V. 6-Dimethylamino-9-(2'-acetylamino-β-D-glucopyranosyl) purine. *J. Org. Chem.* 1954, 19, 1786–1792). In view of this approach, tetra-O-acetyl-D-lyxofuranose (compound 2b) and tetra-O-acetyl-L-lyxofuranose (compound 2a) were prepared for use as the glycosyl-donor in an analogous condensation.

Starting with commercially available D-lyxose, tetra-O-acetyl-D-lyxofuranose (compound 2b) was prepared in three steps using a procedure developed by Guthrie and Smith (see Koszalka, G. W.; Chamberlain, S. D.; Daluge, S. M.; Boyd, F. L.; Tidwell, J. H.; Martin, M. T.; Harvey, R. J.; Frick, L. W.; Perkins, D. G.; Wang, L. H.; Drach, J. C.; Townsend, L. B.; Biron, K. K. Benzimidazoles for the treatment of human cytomegalovirus infection. In *XII International Roundtable: Nucleosides, Nucleotides and their Biological Applications,* La Jolla, Calif., September 1996). After carrying out this synthesis as reported, a 3:1 mixture of the furanose and pyranose isomers, respectively, was obtained as determined by $^1$H NMR. To further optimize conditions in favor of the furanose isomer, both Dowex-50 acidic ion-exchange resin, and acetyl chloride were substituted for sulfuric acid in the first step of this procedure. Substituting these new conditions into the three step procedure resulted in a furanose/pyranose ratio of 1.5:1 (dowex) and 5:1 (acetyl chloride) as determined by $^1$H NMR. Since the pyranose isomer was formed in each case, the sulfuric acid or acetyl chloride conditions proved sufficient and, after silica gel chromatography, compound 2b could be obtained in about a 50% overall yield as a mixture of anomers.

Using a method analogous to that used for the preparation of TCRB (see Townsend, L. B.; Devivar, R. V.; Turk, S. T.; Nassiri, M. R.; Drach, J. C. Design, Synthesis, and Antiviral Activity of Certain 2,5,6-Trihalo-1-(β-D-Ribofuranosyl) benzimidazoles. *J. Med. Chem.* 1995, 38, 4098–4105 and Kawashima, E.; Gupta, P. K.; Devivar, R. V.; Townsend, L. B. 2,5,6-Trichlorobenzimidazole. In *Nucleic Acid Chemistry; part 4,* ; Townsend, L. B., Tipson, R. S., Eds.; John Wiley and Sons: New York, 1991, p 24–26). 2,5,6-trichlorobenzimidazole (TCB, compound 1, see Kawashima, E.; Gupta, P. K.; Devivar, R. V.; Townsend, L. B. 2,5,6-Trichlorobenzimidazole. In *Nucleic Acid Chemistry; part 4,* ; Townsend, L. B., Tipson, R. S., Eds.; John Wiley and Sons: New York, 1991, p 24–26) was silylated with bis (trimethylsilyl)acetamide (BSA, see Vorbruggen, H.; Hofle, G. On the Mechanism of Nucleoside Synthesis. *Chem. Ber.* 1981, 114, 1256–1268) in dry acetonitrile, and then glycosylated with compound 2b in the presence of trimethylsilyl trifluoromethanesulfonate (TMSOTf) to give compound 3b, 1-(2',3',5'-tri-O-acetyl-α-D-lyxofuranosyl)-2,5,6-trichlorobenzimidazole. Compound 3a, 1-(2',3',5'-tri-O-acetyl-α-L-lyxofuranosyl)-2,5,6-trichlorobenzimidazole was prepared in an analogous fashion.

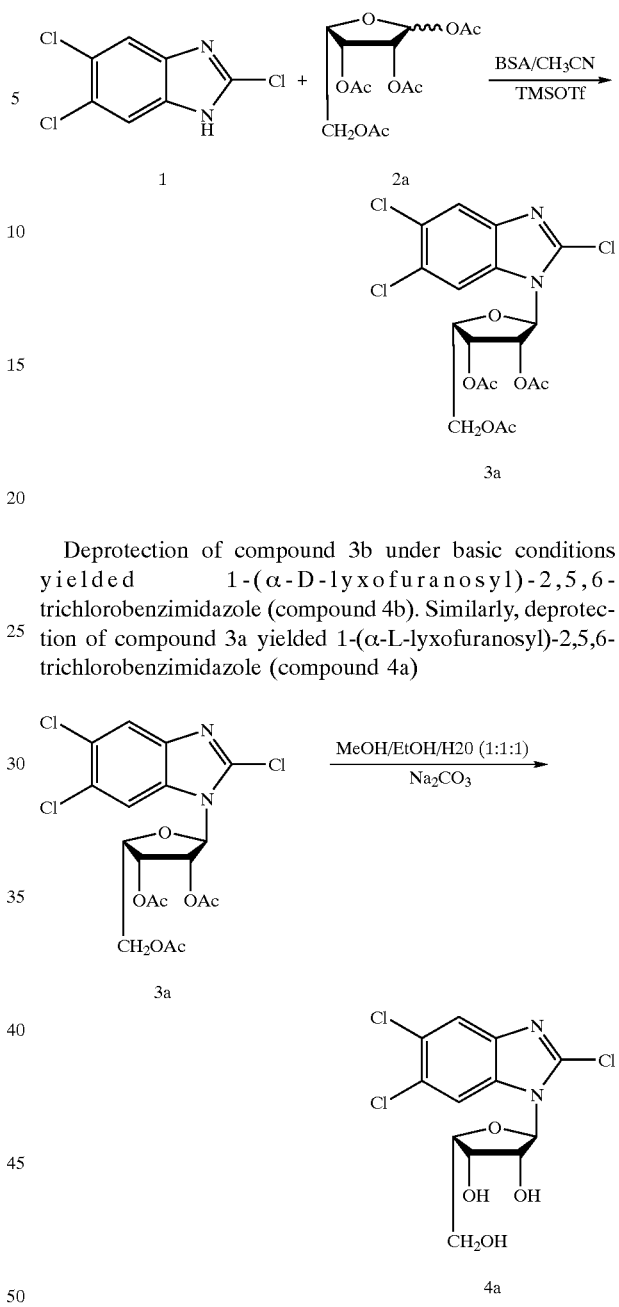

Deprotection of compound 3b under basic conditions yielded 1-(α-D-lyxofuranosyl)-2,5,6-trichlorobenzimidazole (compound 4b). Similarly, deprotection of compound 3a yielded 1-(α-L-lyxofuranosyl)-2,5,6-trichlorobenzimidazole (compound 4a)

As reported previously (see Harrison, D.; Ralph, J. T. Nucleophilic Substitution Reaction of 2-Chlorobenzimidazoles. Part 1. Formation of Benzimidazolin-2-ones and 2-Alkoxybenzimidazoles. *J. Chem. Soc.* 1965, 236–239), the 2-chloro substituent of 1-substituted 2,5,6-trichlorobenzimidazoles can be conveniently displaced by a variety of nucleophiles. Following this approach, compound 3b was treated with anhydrous hydrogen bromide in dichloromethane and subsequently deprotected under basic conditions to give 2-bromo-5,6-dichloro-1-(α-D-lyxofuranosyl)benzimidazole (compound 5b). Similar treatment of compound 3a yielded 2-bromo-5,6-dichloro-1-(α-L-lyxofuranosyl)benzimidazole (compound 5a).

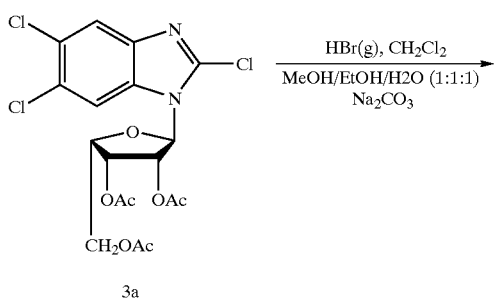

3a

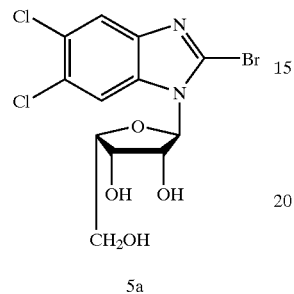

5a

Additionally, the methylamino derivative, 1-(α-D-lyxofuranosyl)-2-methylamino-5,6-dichloro-benzimidazole (compound 6b), was prepared in one step by treatment of compound 3b with 33% methylamine/ethanol in a sealed vessel. Compound 6a, 1-(α-L-lyxofuranosyl)-2-methylamino-5,6-dichloro-benzimidazole, was prepared in a similar fashion from compound 3a.

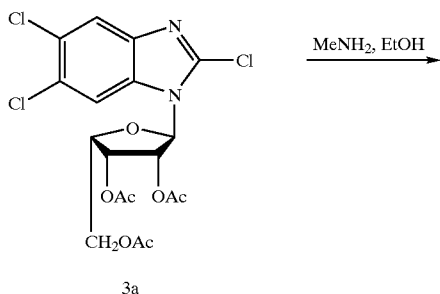

Preparation of the isopropylamino derivative, 1-(α-D-lyxofuranosyl)-2-isopropylamino-5,6-dichloro-benzimidazole (compound 7b) and the cyclopropylamino derivative, 1-(α-D-lyxofuranosyl)-2-cyclopropylamino-5,6-dichloro-benzimidazole (compound 8b), was conveniently accomplished by treating the deprotected nucleoside, compound 4b, with the appropriate primary amine in ethanol. In an analogous fashion, 1-(α-L-lyxofuranosyl)-2-isopropylamino-5,6-dichloro-benzimidazole (compound 7a) and 1-(α-L-lyxofuranosyl)-2-cyclopropylamino-5,6-dichloro-benzimidazole (compound 8a) were prepared from compound 4a.

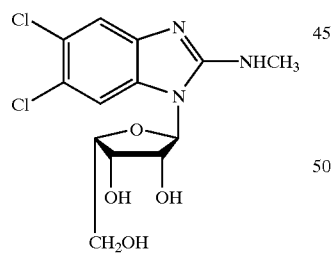

7a: R = C₃H₇
8a: R = C₃H₅

Additionally, the 2-thio derivative, 1-(α-D-lyxofuranosyl)-2-thio-5,6-dichloro-benzimidazole (compound 9b), was prepared by heating compound 4b in an ethanol/thiourea mixture at reflux temperature for 19 hours. Compound 9a, 1-(α-L-lyxofuranosyl)-2-thio-5,6-dichloro-benzimidazole was prepared in a similar fashion.

Compound 9b was also prepared starting with commercially available 5,6-dichlorobenzimidazole-2-thione (compound 10, see Devivar, R. V.; Kawashima, E.; Revankar, G. R.; Breitenbach, J. M.; Kreske, E. D.; Drach, J. C.; Townsend, L. B. Benzimidazole Ribonucleosides: Design, Synthesis, and Antiviral Activity of Certain 2-(Alkylthio)- and 2-(Benzylthio)-5,6-dichloro-β-D-ribofuranosyl)benzimidazoles. *J. Med. Chem.* 1994, 37, 2942–2948), which was silylated with BSA in dry acetonitrile and then glycosylated with compound 2b in the presence of TMSOTf to give compound 9b, after deprotection. This result unequivocally establishes the site of glycosylation as having occurred at N-1 and not at the 2-thio moiety. Compound 9a was also similarly prepared.

14 was subsequently reacted with isopropylamine in ethanol to yield 2-isopropylamino-5,6-dichloro-1-(β-L-lyxofuranosyl)benzimidazole (compound 15).

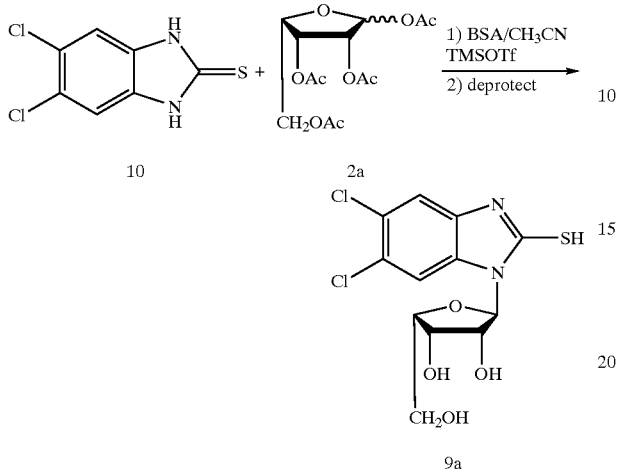

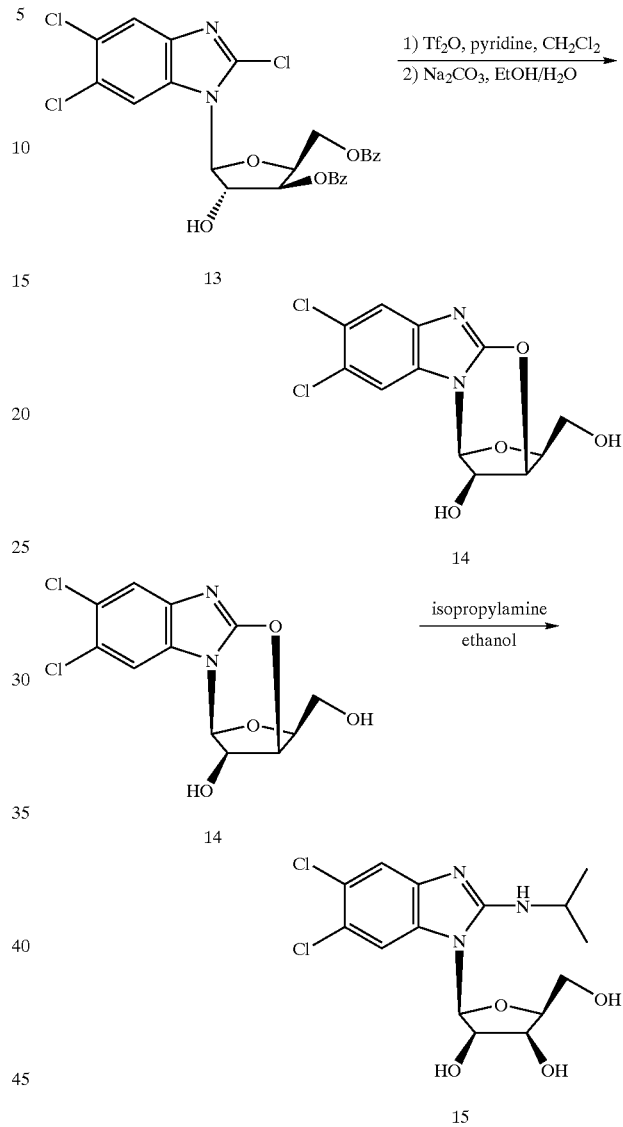

Finally, treatment of compound 9b with NH$_4$OH in acetonitrile/water, followed by alkylation with benzyl bromide or methyl iodide, gave 2-benzylthio-5,6-dichloro-1-(α-D-lyxofuranosyl)benzimidazole (compound 11b) and 5,6-dichloro-1-(α-D-lyxofuranosyl)-2-(methylthio) benzimidazole (compound 12b), respectively. In a similar fashion, 2-benzylthio-5,6-dichloro-1-(α-L-lyxofuranosyl)-benzimidazole (compound 11a) and 5,6-dichloro-1-(α-L-lyxofuranosyl)-2-(methylthio)benzimidazole (compound 12a) were obtained from compound 9a.

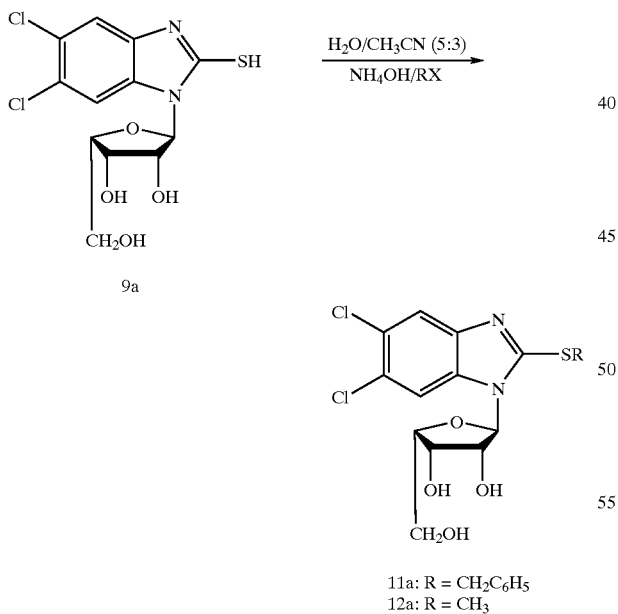

In another approach, a β-L-analog was prepared by first forming 2,5,6-trichloro-1-(3',5'-di-O-benzoyl-β-L-xylofuranosyl)benzimidazole (compound 13) using hydrazine hydrate, pyridine, and acetic acid. Compound 13 was then reacted with triflic anhydride and pyridine in dichloromethane to obtain 2,3'-O-cyclo-5,6-dichloro-1-(β-L-lyxofuranosyl) benzimidazole (compound 14). Compound The anomeric configuration of each of the compounds was assigned according to Baker's rules (see Baker, B. R.; Joseph, J. P.; Schaub, R. E.; Williams, J. H. Puromycin Synthetic Studies. V. 6-Dimethylamino-9-(2'-acetylamino-β-D-glucopyranosyl)purine. *J. Org. Chem.* 1954, 19, 1786–1792), and confirmed by NOE experiments (see Rosemeyer, H.; Toth, G.; Seela, F. Assignment of Anomeric Configuration of D-Ribo-,Arabino-,2'-Deoxyribo-, and 2',3'-Dideoxyribonucleotides by NOE Difference Spectroscopy. *Nucleosides, Nucleotides* 1989, 8, 587–597).

Thus, in one embodiment, the present invention pertains to a process for the preparation of a D- or L-lyxofuranosyl benzimidazole compound of the present invention, said process comprising the steps of:

(a) reacting a compound of formula (II) with a compound of formula (III),

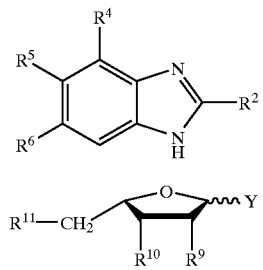

wherein $R_2$ is selected from the group consisting of —Cl, —Br and =S, and each of $R^9$, $R^{10}$ or $R^{11}$ is independently the same or different and is —H or a hydroxyl protecting group; and, (b) subsequently performing one or more of the following steps:
  (i) removing one or more hydroxyl protecting groups from the product of (a), if present;
  (ii) reacting the product of (a) with HX, wherein X is selected from the group consisting of —Cl, —Br, —F and —I;
  (iii) reacting the product of (a) with $R^8NH_2$, wherein $R^8$ is —H or a linear, branched, or cyclic alkyl group having 1–6 carbon atoms;
  (iv) reacting the product of (a) with $H_2NCSNH_2$;
  (v) reacting the product of (a) with $C_6H_5CH_2X$, wherein X is selected from the group consisting of —Cl, —Br, —F and —I;
  (vi) reacting the product of (b)(iv) with $C_6H_5CH_2X$, wherein X is selected from the group consisting of —Cl, —Br, —F and —I;
  (vii) reacting the product of (a) with $CH_3I$; and,
  (viii) reacting the product of (b)(iv) with $CH_3I$.

General Chemical Methods

Melting points were determined on a Thomas-Hoover apparatus and are uncorrected. Silica gel, SilicAR 40–63 microns 230–400 mesh (Mallinckrodt) was used for chromatography. Thin-layer chromatography (TLC) was performed on prescored SilicAR 7GF plates (Analtech, Newark, Del.). TLC plates were developed in the following solvent systems: system 1 (2% MeOH/CHCl$_3$, v/v), system 2 (10% MeOH/CHCl$_3$, v/v), system 3 (35% EtOAc/hexanes, v/v), system 4 (25% EtOAc/hexanes, v/v), system 5 (5% MeOH/CHCl$_3$, v/v), system 6 (15% MeOH/CHCl$_3$, v/v), system 7 (20% EtOAc/hexanes, v/v), and system 8 (50% EtOAc/hexanes, v/v). Compounds were visualized by illuminating with UV light (254 nm) or by treatment with 10% methanolic sulfuric acid followed by charring on a hot plate. Evaporations were carried out under reduced pressure (water aspirator) with the bath temperature not exceeding 45° C., unless specified otherwise. $^1$H NMR spectra were recorded on either a Bruker 200, 300, 360, or 500 MHz instrument. The chemical shifts are expressed in parts per million relative to the standard chemical shift of the solvent DMSO-d$_6$ (d=2.50). All $^1$H NMR assignments reported were made by homonuclear decoupling experiments, except compound 6a, which was assigned by a COSY experiment. Microanalytical results (which are summarized in Table 1) were performed by the University of Michigan, Department of Chemistry, and are within ±0.4% of the theoretical values, unless otherwise specified. Unless otherwise noted, all materials were obtained from commercial suppliers.

EXAMPLES

Several antiviral compounds of the present invention are described in the following examples, which are offered by way of illustration and not by way of limitation.

Compound 3a 1-(2,3,5-Tri-O-acetyl-α-L-lyxofuranosyl)-2,5,6-trichlorobenzimidazole A 500 mL round-bottom flask equipped with a claisen adapter and stirrer was evacuated and backflushed with argon. 2,5,6-trichlorobenzimidazole (see Kawashima, E.; Gupta, P. K.; Devivar, R. V.; Townsend, L. B. 2,5,6-Trichlorobenzimidazole. In *Nucleic Acid Chemistry;* part 4, ; Townsend, L. B., Tipson, R. S., Eds.; John Wiley and Sons: New York, 1991, p 24–26) (compound 1, 1.74 g, 7.85 mmoles) was then suspended in dry CH$_3$CN (100 mL) and bis(trimethylsilyl) acetamide (1.94 mL, 8.84 mmoles) was added dropwise via a syringe at which time the heterocycle went into solution. A solution of 1,2,3,5-tetra-O-acetyl-L-lyxofuranose (see Kam, B. L.; Barascut, J.-L.; Imbach, J.-L. A General Method of Synthesis and Isolation, and an N.M.R.—Spectroscopic Study, of Tetra-O-acetyl-D-aldopentofuranoses. *Carbohydrate Res.* 1979, 69, 135–142) (compound 2a, 3.25 g, 10.2 mmoles) dissolved in CH$_3$CN (50 mL) was added to the stirred solution, and this was followed immediately by TMSOTf (1.8 mL, 9.3 mmoles). After 20 hours the solvent was evaporated under reduced pressure to afford a yellow residue. This residue was dissolved in ethyl acetate (100 mL), and washed successively with water, NaHCO$_3$ (sat.), and then brine (1×75 mL each). The organic layer was dried over magnesium sulfate and the solvent was evaporated under reduced pressure to yield a yellow oil. This oil was subjected to column chromatography (3×25 cm, solvent system 3), and the appropriate fractions were combined to yield 2.59 g (67%) of compound 3a as a yellow glass. This glass was used without further purification in subsequent reactions. R$_f$=0.80 (solvent system 1). $^1$H NMR (DMSO-d$_6$): δ8.19 (s, 1H), 8.00 (s, 1H), 6.28 (d, 1H, J=7.9 Hz), 5.97 (m, 1 H), 5.74 (m, 1H), 5.17 (m, 1H), 4.26 (m, 2H), 2.19 (s, 3H), 2.03 (s, 3H), 1.96 (s, 3H). HRMS calcd for CHN: M$^+$, 478.0101. Found: 478.0098 (M$^+$).

Compound 3b 1-(2,3,5-Tri-O-acetyl-α-D-lyxofuranosyl)-2,5,6-trichlorobenzimidazole The procedure is the same as that described for compound 3a, except that compound 2b was used instead of compound 2a. The TLC (co-spots in solvent system 3) and proton spectrum were identical to that obtained for compound 3a. Yield: 3.40 g (88%) as a yellow glass. HRMS calcd for CHN: M$^+$, 478.0101. Found: 478.0085 (M$^+$).

Compound 4a 1-(α-L-Lyxofuranosyl)-2,5,6-trichlorobenzimidazole

A 100 mL round bottom flask was charged with compound 3a (303 mg, 0.65 mmole) which was then dissolved in 50 mL of an equimolar mixture (v/v) of ethanol and water. Anhydrous sodium carbonate (212 mg, 2.0 mmoles)was added to the stirred solution and then the reaction mixture was allowed to stir at room temperature for an additional 3 hours. Acetic acid (2 mL) was added and the solvent was evaporated under reduced pressure. The resultant solid was dissolved in ethyl acetate and the solution was washed successively with water, NaHCO$_3$ (sat.), and brine (1×50 mL each). The organic layers were collected and dried over sodium sulfate. The solvent was evaporated under reduced pressure to yield, upon vacuum drying, 205 mg (89%) of compound 4a as a white foam. $R_f$=0.30 (solvent system 2). Mp: 184–185° C. $^1$H NMR (DMSO-$d_6$) δ7.98 (s, 1H), 7.92 (s, 1H), 5.64 (d, 1H, J=9.3 Hz), 5.49 (d, 1H, J=3.2 Hz, $D_2O$ exchangeable), 5.40 (d, 1H, J=3.8 Hz, $D_2O$ exchangeable), 5.27 (d, 1H, J=6.5 Hz, $D_2O$ exchangeable), 4.25 (m, 1H), 4.02 (d, 1H, J=11.6 Hz), 3.92 (m, 1H), 3.79 (d, 1H, J=12.4Hz), 3.71 (m, 1H). HRMS calcd for $C_{12}H_{11}O_4N_2Cl_3$: $M^+$, 351.9784. Found: 351.9782 ($M^+$). Anal. ($C_{12}H_{11}O_4N_2Cl_3$) C, H, N.

Compound 4b 1-(α-D-Lyxofuranosyl)-2,5,6-trichlorobenzimidazole

The procedure is the same as that described for compound 4a, except compound 3b (632 mg, 1.07 mmoles) was used instead of compound 3a. The TLC (co-spots in solvent systems 1 and 2) and proton spectrum were identical to that obtained for compound 4a. Yield: 175 mg (76%) as a white foam. Mp: 175–176° C. HRMS calcd for $C_{12}H_{11}O_4N_2Cl_3$: $M^+$, 351.9784. Found: 351.9773 ($M^+$). Anal. ($C_{12}H_{11}O_4N_2Cl_3 \cdot H_2O$) C, H, N.

Compound 5a

2-Bromo-5,6dichloro-1-(α-L-lyxofuranosyl)benzimidazole

A 3-neck round bottom flask was charged with compound 3a (460 mg, 0.96 mmoles) and dichloromethane (50 mL). Anhydrous hydrogen bromide was slowly bubbled into the solution for 40 minutes while the mixture was stirred at room temperature, and then the gas was turned off for 90 minutes, at which time the gas was turned back on and a white precipitate formed. The hydrogen bromide was turned off again after 135 minutes and the mixture was allowed to stir for an additional 3 hours. At this time $NaHCO_3$ (sat.) was added slowly until the evolution of gas ceased. The clear solution was then washed with $NaHCO_3$ (sat., 50 mL), brine (50 mL), and dried over magnesium sulfate. The solvent was evaporated and co-evaporated with diethyl ether under reduced pressure to yield a yellow glass. $R_f$=0.80 (solvent system 1). $^1$H NMR (DMSO-$d_6$): δ8.18 (s, 1H), 8.01 (s, 1H), 6.25 (d, 1H, J=7.8 Hz), 5.97 (m, 1H), 5.74 (m, 1H), 5.17 (m, 1H), 4.26 (m, 2H), 2.19 (s, 3H), 2.03 (s, 3H), 1.97 (s, 3H). The yellow glass was then dissolved in a stirred (1:1:1) solution of ethanol, MeOH and water (50 mL). The solution was then charged with sodium carbonate (380 mg, 3.6 mmoles). After 100 min., glacial acetic acid (0.5 mL) was added and the alcohol was evaporated under reduced pressure. An additional 25 mL of cold water was added and the mixture was filtered. The resulting solid was recrystallized from methanol/water and dried at 78° C. under reduced pressure for 2 days to give 194 mg (64%) of compound 5a as white crystals. $R_f$=0.06 (solvent system 5), $R_f$=0.30 (solvent system 1). Mp: 178–179° C. $^1$H NMR (DMSO-$d_6$): δ8.00 (s, 1H), 7.91 (s, 1H), 5.96 (d, 1H, J=8.1 Hz), 5.58 (d, 1H, J=6.6 Hz, $D_2O$ exchangeable), 5.29 (d, 1H, J=4.3 Hz, $D_2O$ exchangeable), 4.71 (m, 2H), 4.59 (m, 1H), 4.19 (m, 1H), 3.65 (m, 2H). HRMS calcd for $C_{12}H_{11}O_4N_2Cl_2Br$: $M^+$, 395.9279. Found: 395.9273 ($M^+$). Anal. ($C_{12}H_{11}O_4N_2Cl_2Br$) C, H, N.

Compound 5b

2-Bromo-5,6-dichloro-1-(α-D-lyxofuranosyl)benzimidazole

The procedure is the same as that described for compound 5a, except that compound 3b was used instead of compound 3a. The TLC (co-spots in solvent system 1) and proton spectrum were identical to that obtained for compound 5a. Yield: 255 mg (84%, two steps) as white crystals. Mp: 178–179° C. HRMS calcd for $C_{12}H_{11}O_4N_2Cl_2Br$: $M^+$, 395.9279. Found: 395.9261 ($M^+$). Anal. ($C_{12}H_{11}O_4N_2Cl_2Br$) C, H, N.

Compound 6a 5,6-Dichloro-1-(α-L-lyxofuranosyl)-2-(methylamino)benzimidazole

A 250 mL pressure bottle was charged with compound 3a (480 mg, 1.00 mmole) and 33% methylamine/absolute ethanol (25 mL). The vessel was sealed and the reaction was stirred at room temperature for 16 hours. The solvent was then evaporated and co-evaporated with hexanes and diethyl ether under reduced pressure. The remaining solid was recrystallized twice from a methanol and water mixture and dried at 78° C. under reduced pressure to yield 259 mg (72%) of compound 6a as a white solid. $R_f$=0.09 (solvent system 1). Mp: 131–132° C. $^1$H NMR (DMSO-$d_6$): δ7.40 (s, 1H), 7.36 (s, 1H), 6.81 (m, 1H, $D_2O$ exchangeable), 5.73 (d, 1H, J=8.1 Hz), 5.27 (d, 1H, J=4.4 Hz, $D_2O$ exchangeable), 5.24 (d, 1H, J=4.3 Hz, $D_2O$ exchangeable), 4.66 (t, 1H, J=5.6, $D_2O$ exchangeable), 4.57 (m, 1H), 4.44 (m, 1H), 4.16 (m, 1H), 3.63 (m, 2H), 2.88 (d, 3H, J=4.40 Hz). Anal. ($C_{13}H_{15}O_4N_3Cl_2$) C, H, N.

Compound 6b 5,6-Dichloro-1-(α-D-lyxofuranosyl)-2-(methylamino)benzimidazole

The procedure is the same as that described for compound 6a, except that compound 3b was used instead of compound 3a. The TLC (co-spots in solvent system 1) and proton spectrum were identical to that obtained for compound 6a. Yield: 223 mg (62%) as a white solid. Mp: 126–128° C. Anal. ($C_{13}H_{15}O_4N_3Cl_2$) C, H, N.

Compound 7a 5,6-Dichloro-2-isopropylamino-1-(α-L-lyxofuranosyl)benzimidazole 1-(α-L-lyxofuranosyl)-2,5,6-trichlorobenzimidazole (compound 4a, 300 mg, 0.85 mmol) was dissolved in ethanol (5 mL) and isopropylamine (10 mL) was then added. The flask was sealed and the reaction mixture stirred at 70° C. for two days. The mixture was then evaporated under reduced pressure, and subjected to silica gel chromatography (3×25 cm.), eluting with solvent system 5. After evaporating the solvent under reduced pressure, the resultant solid was stirred in 10 mL of benzene for 12 hours and then collected by filtration. The solid was dried under reduced pressure at 78° C. for 2 days to give 202 mg (63%) of analytically pure compound 7a. Mp: 198–201° C. $^1$H NMR (DMSO-$d_6$): δ7.40 (s, 1H), 7.32 (s, 1H), 6.57 (bs, 1H, $D_2O$ exchangeable), 5.79 (m, 1H), 5.28 (m, 1H, $D_2O$ exchangeable), 5.21 (m, 1H, $D_2O$ exchangeable), 4.67 (bs, 2H, $D_2O$ exchangeable), 4.54 (m, 1H), 4.42 (m, 1H), 4.17 (m, 1H), 4.03 (m, 1H), 3.68 and 3.59 (m, 2H), 1.21 (bs, 6H). Anal. ($C_{15}H_{19}O_4N_3Cl_2$) C, H, N.

Compound 7b 5,6-Dichloro-2-isopropylamino-1-(α-D-lyxofuranosyl)benzimidazole

The procedure is the same as that described for compound 7a, except that compound 4b (274 mg, 0.77 mmoles) was used instead of compound 4a. The TLC (co-spots in solvent system 1) and proton spectrum were identical to that obtained for compound 7a. Yield 205 mg (64%) as a white solid. Mp: 201–202° C. Anal. ($C_{15}H_{19}O_4N_3Cl_2$) C, H, N.

Compound 8a

2-Cyclopropylamino-5,6-dichloro-1-(α-L-lyxofuranosyl)benzimidazole

The procedure is the same as that described for compound 7a, except that cyclopropylamine was used instead of isopropylamine, and compound 4a (300 mg, 0.80 mmoles) was used. Yield 299 mg (65%) as a white solid. Mp: 184–186° C. $^1$H NMR (DMSO-$d_6$): δ7.47 (s, 1H), 7.36 (s, 1H), 7.05 (bs, 1H, $D_2O$ exchangeable), 5.72 (m, 1H), 5.24 (m, 1H, $D_2O$ exchangeable), 5.17 (m, 1H, $D_2O$ exchangeable), 4.65 (bs, 2H, $D_2O$ exchangeable), 4.53 (m, 1H), 4.42 (m, 1H), 4.15 (m, 1H), 3.66 and 3.57 (m, 2H), 0.86 (m, 2H), 0.57 (m, 1H), 0.50 (m, 1H). Anal. ($C_{15}H_{17}O_4N_3Cl_2$) C, H, N.

Compound 8b

2-Cyclopropylamino-5,6-dichloro-1-(α-D-lyxofuranosyl)benzimidazole

The procedure is the same as that described for compound 7a, except that cyclopropylamine was used instead of isopropylamine, and compound 4b (248 mg, 0.66 mmoles) was used instead of compound 4a. The TLC (co-spots in solvent system 1) and proton spectrum were identical to that obtained for compound 8a. Yield 247 mg (67%) as a white solid. Mp: 183–185° C. Anal. ($C_{15}H_{17}O_4N_3Cl_2$) C, H, N.

Compound 9a 5,6-Dichloro-1-(α-L-lyxofuranosyl)benzimidazol-2-thione

Method A: A 500 mL round bottom flask equipped with a claisen adapter and a stirrer was evacuated and back-flushed with argon. Dry 5,6-dichlorobenzimidazol-2-thione (compound 10, 1.53 g, 7.0 mmoles) was then suspended in $CH_3CN$ (80 mL). Bis(trimethylsilyl)acetamide (1.95 mL, 7.9 mmoles) was added dropwise via a syringe and the mixture was heated until the heterocycle went into solution (30–40 C.). Compound 2a (see Kam, B. L.; Barascut, J.-L.; Imbach, J.-L. A General Method of Synthesis and Isolation, and an N.M.R.-Spectroscopic Study, of Tetra-O-acetyl-D-aldopentofuranoses. *Carbohydrate Res.* 1979, 69, 135–142) (2.5 g, 7.9 mmoles) dissolved in $CH_3CN$ (40 mL) was added to the stirred solution followed immediately by TMSOTf (1.5 mL, 7.9 mmoles). After 24 hours, the solvent was evaporated under reduced pressure and the remaining residue was subjected to silica gel chromatography (3×25 cm.) eluting first with solvent system 4, and then solvent system 3. Both compound 10 (40 mg) and the protected nucleoside (2.84 g, 87% based on consumed heterocycle) were obtained as separate compounds. $R_f$=0.45 (compound 10, solvent system 3). $^1$H NMR (DMSO-$d_6$): δ13.33 (bs, 1H), 7.93 (s, 1H), 7.41 (s, 1H), 6.75 (d, 1H, J=8.3 Hz), 6.13 (m, 1H), 5.74 (m, 1H), 5.13 (m, 1H), 4.23 (m, 2H), 2.19 (s, 3H), 2.03 (s, 3H), 1.94 (s, 3H).

A 200 mL round bottom flask was charged with the protected nucleoside (2.75 g, 5.66 mmoles) and dissolved in 92% ethanol/water (50 mL, v/v). Sodium carbonate (4.0 g, 37 mmoles) was added to this stirred solution, and the reaction mixture was allowed to stir at room temperature for 24 hours. Acetic acid (2 mL) was added and then the ethanol was evaporated under reduced pressure. The resulting mixture was taken up in an additional 275 mL of cold water and extracted with EtOAc (15×50 mL). The solvent was then evaporated under reduced pressure. The resulting solid was recrystallized from methanol and dried under reduced pressure at 78° C. for 2 days to give 1.48 g (74%) of 9a as white crystals. $R_f$=0.27 (solvent system 2). Mp: 235–236° C. $^1$H NMR (DMSO-$d_6$): δ13.15 (bs, 1H, $D_2O$ exchangeable, NH), 7.62 (s, 1H, H7 or H4), 7.40 (s, 1H, H4 or H7), 6.46 (d, 1H, J=8.2 Hz, H1'), 5.31 (d, 1H, J=6.7 Hz, $D_2O$ exchangeable, 2'-OH), 5.15 (d, 1H, J=3.8 Hz, $D_2O$ exchangeable, 3'-OH), 4.81 (m, 1H, H2'), 4.67 (t, 1H, J=4.1, 5'-OH), 4.67 (m, 1H, H4'), 4.50 (m, 1H, H3'), 3.61 (m, 2H, H5'a and H5'b). Anal. ($C_{12}H_{12}O_4N_2Cl_2S$) C, H, N.

Method B: A 10 mL round bottom flask was charged with compound 4a (42 mg, 0.12 mmoles), thiourea (36 mg, 0.48 mmoles), and absolute ethanol (2 mL). The reaction mixture was heated at reflux temperature for 19 hours, the solvent evaporated under reduced pressure, and then the resultant residue was triturated with 5 mL of water. After standing for 3 hours, the solid was collected by filtration and dried under reduced pressure at 60° C. for 48 hours to yield 30 mg (71%) of a white product. The TLC (co-spots in solvent system 2) and proton spectrum were identical to that obtained for compound 9a (Method A). Mp: 234–236° C.

Compound 9b 5,6-Dichloro-1-(α-D-lyxofuranosyl)benzimidazol-2-thione

The procedure is the same as that described for compound 9a (Method A), except that compound 2b (see Kam, B. L.; Barascut, J.-L.; Imbach, J.-L. A General Method of Synthesis and Isolation, and an N.M.R.-Spectroscopic Study, of Tetra-O-acetyl-D-aldopentofuranoses. *Carbohydrate Res.* 1979, 69, 135–142) was used instead of compound 2a. The TLC (co-spots in solvent system 2) and proton spectrum were identical to that obtained for compound 9a (Method A and B). The yield on the first step was 91% (based on consumed heterocycle), and the yield on second step was quantitative (2.0 g). An analytical sample was prepared by recrystallization from methanol and drying as in 9a. Mp: 234–236° C. Anal. ($C_{12}H_{12}O_4N_2Cl_2S$) C, H, N.

Compound 11a

2-Benzylthio-5,6-dichloro-1-(α-L-lyxofuranosyl)benzimidazole

A 100 mL round bottom flask was charged with compound 9a (351 mg, 1.0 mmole), $H_2O$ (25 mL) and $CH_3CN$ (15 mL). To the suspension, 12 drops of concentrated ammonium hydroxide was added to effect a solution. Benzyl bromide (0.12 mL, 1.0 mmole) was then added and the mixture stirred at room temperature for 16 hours. The excess acetonitrile was then evaporated under reduced pressure, and the aqueous layer was extracted with EtOAc (2×40 mL). The organic extracts were combined, dried ($MgSO_4$), and the solvent evaporated to yield 410 mg (93%) of a white solid. This was subsequently recrystallized from methanol/water and dried under reduced pressure at 78° C. for 2 days to yield 361 mg (82%) of compound 11a as white crystals. Mp: 210–212° C. $^1$H NMR (DMSO-$d_6$): δ7.89 (s, 1H), 7.78 (s, 1H), 7.37 (m, 5H), 5.80 (d, 1H, J=7.9 Hz), 5.51 (d, 1H, J=7.3 Hz, $D_2O$ exchangeable), 5.26 (d, 1H, J=4.2 Hz, $D_2O$ exchangeable), 4.67 (t, 1H, J=5.7), 4.62 (m, 3H), 4.50 (m, 1H), 4.15 (m, 1H), 3.60 (m, 2H). Anal. ($C_{19}H_{18}O_4N_2Cl_2S$) C, H, N.

Compound 11b

2-Benzylthio-5,6-dichloro-1-(α-D-lyxofuranosyl)benzimidazole

The procedure is the same as that described for compound 11a, except that compound 9b was used instead of compound 9a. The TLC (co-spots in solvent system 1) and proton spectrum were identical to that obtained for compound 11a. Yield: 207 mg (47%) as white crystals. Mp: 196–198° C. Anal. ($C_{19}H_{18}O_4N_2Cl_2S$) C, H, N.

Compound 12a

5,6-Dichloro-1-(α-L-lyxofuranosyl)-2-(methylthio)benzimidazole

The procedure is the same as that described for compound 11a, except that methyl iodide (0.06 mL, 1.0 mmole) was used instead of benzylbromide. Yield: 305 mg (84%) of compound 12a as white crystals. Mp: 210–212° C. $^1$H NMR (DMSO-$d_6$): δ7.86 (s, 1H), 7.77 (s, 1H), 5.80 (d, 1H, J=8.1 Hz), 5.52 (d, 1H, J=7.1 Hz, $D_2O$ exchangeable), 5.28 (d, 1H, J=3.6 Hz, $D_2O$ exchangeable), 4.70 (t, 1H, J=5.6, $D_2O$ exchangeable), 4.63 (m, 1H, H3'), 4.52 (m, 1H), 4.17 (m, 1H), 3.63 (m, 2H). Anal. ($C_{13}H_{14}O_4N_2Cl_2S$) C, H, N.

Compound 12b

5,6-Dichloro-1(α-D-lyxofuranosyl)-2-(methylthio)benzimidazole

The procedure is the same as that described for compound 11b, except that methyl iodide (0.06 mL, 1.0 mmole) was used instead of benzylbromide. The TLC (co-spots solvent system 1) and proton spectrum were identical to that obtained for compound 12a. Yield: 142 mg (39%) as white crystals. Mp: 204–206° C. Anal. ($C_{13}H_{14}O_4N_2Cl_2S$) C, H, N.

Compound 14

2,3'-O-Cyclo-5,6-dichloro-1-(β-L-lyxofuranosyl)benzimidazole

Triflic anhydride (trifluoromethanesulfonic anhydride, 0.37 mL, 2.2 mmol) in a solution of dichloromethane (4.5 mL) was added to a solution of 2,5,6-trichloro-1-(3',5'-di-O-benzoyl-β-L-xylofuranosyl)benzimidazole (compound 13, 820 mg, 1.5 mmol) in a mixture of dichloromethane (7.5 mL) and pyridine (0.75 mL). The reaction mixture was stirred at 0° C. and monitored by TLC. After 30 min, water (1.5 mL) was added and the temperature of the reaction mixture was increased to 40° C. After an additional 15 hours of stirring, the mixture was diluted with dichloromethane (10 mL) and water (10 mL). The organic extract was washed with water (5 mL), dried over anhydrous sodium sulfate, filtered and the filtrate was evaporated to dryness. The residue was subjected to silica gel chromatography (2.5×15 cm, eluent: gradient of methanl (0–2%) in dichloromethane) to give one major compound ($R_f$: 0.40, 590 mg) as a foam. $^1$H NMR (DMSO-$d_6$): δ7.9–7.5 (m, 12H, phenyls, H-4 and H-7), 6.61 (d, 1H, H-1', J=5.4 Hz), 6.27 (t, 1H, H-2', J=5.5 Hz), 5.88 (t, 1H, H-3', J=5.5 Hz), 4.9 (m, 1H, H-4'), 4.6–4.5 (m, 1H, H-5'), 4.3–4.2 (m, 1H, H-5").

This foam was dissolved in a solution of ethanol and water (9:1, v/v, 20 mL) and sodium carbonate (0.45 g, 4.2 mmol) was added. The reaction mixture was stirred 4 days, then acetic acid (1 mL) was added and the mixture was evaporated to dryness. Water (10 mL) and ethyl acetate (20 mL) were added to the residue. The organic extract was washed with water (2×5 mL), dried over sodium sulfate, filtered, and the filtrate was evaporated to dryness. The residue was suspended in boiling dichloromethane (10 mL) and methanol was added until complete dissolution had occurred. Compound 14 (200 mg, 43%) crystallized from this solution. Mp: 255–257° C. (decomp.). $R_f$: 0.18. $^1$H NMR (DMSO-$d_6$): δ7.96 and 7.62 (2 s, 2H, H-4 and H-7), 6.36 (d, 1H, OH-2', J=2.9 Hz), 6.18 (d, 1H, H-1', J=4.0 Hz), 5.04 (t, 1H, H-3', J=2.9 Hz), 5.01 (t, 1H, OH-5'), J=5.4 Hz), 4.7 (m, 1H, H-2'), 4.4 (m, 1H, H-4'), 3.5–3.4 (m, 1H, H-5'), 3.4–3.3 (m, 1H, H-5"). Anal. ($C_{12}H_{10}Cl_2N_2O_4$) C, H, N.

Compound 15

2-isopropylamino-5,6-dichloro-1-(β-L-lyxofuranosyl)benzimidazole

Compound 14 (150 mg, 0.47 mmol) was dissolved in ethanol (3.3 mL). Isopropylamine (2.0 mL, 24 mmol) was added, the flask was sealed and the reaction mixture stirred at 70° C. for one week. At this time, the reaction was checked by TLC. Because only a partial reaction had occurred, the reaction mixture was stirred at 80° C. for an additional week. The mixture was then evaporated to dryness and the residue was dissolved in ethyl acetate (20 mL) and water (5 mL). The organic extract was washed with water (2×5 mL), dried over $Na_2SO_4$, filtered and the filtrate was evaporated to dryness. The residue was subjected to silica gel chromatography (2.5×15 cm, eluent: methanol (6%) in dichloromethane). Fractions that contained the major spot ($R_f$: 0.24) were evaporated to dryness. The resulting solid was suspended in boiling dichloromethane (5 mL) and methanol was added until complete dissolution occurred. Compound 15 (127 mg, 71%) crystallized from this solution. $R_f$: 0.24. Mp: 197–199° C. $^1$H NMR (DMSO-$d_6$): δ7.60 and 7.31 (2 s, 2H, H-4 and H-7), 7.21 (d, 1H, NH, J=7.1 Hz), 6.02 (d, 1H, H-1', J=6.6 Hz), 5.84 (bs, 1H, OH-3', J=2.9 Hz), 5.32 (d, 1H), OH-2'), J=5.9 Hz), 4.85 (t, 1H, OH-5', J=4.9 Hz), 4.4 (m, 1H, H-2'), 4.2 (bs, 1H, H-3'), 4.0–3.9 (m, 1H, C$\underline{H}$(CH$_3$)$_2$), 3.7–3.7 (m, 3H, H-4', H-5' and H-5"), 1.18 (d, 6H, CH(C$\underline{H}_3$)$_2$, J=6.4 Hz). Anal. ($C_{15}H_{19}Cl_2N_3O_4$) C, H, N.

TABLE 1

Microanalysis Results: Calculated and Found

| | Calcd | | | Found | | |
|---|---|---|---|---|---|---|
| Cmpd | C | H | N | C | H | N |
| 4a | 40.76 | 3.14 | 7.92 | 40.78 | 3.28 | 7.75 |
| 4b.H$_2$O | 39.20 | 3.60 | 7.07 | 38.79 | 3.80 | 7.54 |
| 5a | 36.21 | 2.79 | 7.04 | 36.30 | 2.89 | 7.03 |
| 5b | 36.21 | 2.79 | 7.04 | 36.34 | 3.07 | 6.69 |
| 6a | 44.84 | 4.34 | 12.07 | 44.92 | 4.51 | 11.91 |
| 6b | 44.84 | 4.34 | 12.07 | 44.98 | 4.27 | 12.08 |
| 7a | 47.89 | 5.09 | 11.17 | 47.82 | 5.24 | 10.82 |
| 7b | 47.89 | 5.09 | 11.17 | 47.79 | 5.02 | 10.90 |
| 8a | 48.14 | 4.58 | 11.23 | 48.49 | 4.62 | 10.90 |
| 8b | 48.14 | 4.58 | 11.23 | 47.83 | 4.62 | 10.90 |
| 9a | 41.04 | 3.44 | 7.98 | 41.02 | 3.52 | 8.11 |
| 9b | 41.04 | 3.44 | 7.98 | 40.66 | 3.48 | 7.90 |
| 11a | 51.71 | 4.11 | 6.35 | 51.36 | 4.05 | 6.11 |
| 11b | 51.71 | 4.11 | 6.35 | 52.00 | 4.19 | 6.45 |
| 12a | 42.75 | 3.86 | 7.67 | 42.90 | 4.04 | 7.61 |
| 12b | 42.75 | 3.86 | 7.67 | 42.67 | 3.88 | 7.51 |
| 14 | 45.45 | 3.18 | 8.83 | 45.08 | 3.15 | 8.74 |
| 15 | 47.89 | 5.09 | 11.17 | 47.91 | 5.08 | 11.02 |

D. Assays for Antiviral Activity and Cytotoxicity

Cell Culture Procedures

The routine growth and passage of KB, BSC-1 and HFF cells was performed in monolayer cultures using minimal essential medium (MEM) with either Hanks salts [MEM(H)] or Earle salts [MEM(E)] supplemented with 10% calf serum or 10% fetal bovine serum (HFF cells). The sodium bicarbonate concentration was varied to meet the buffering capacity required. Cells were passaged at 1:2 to 1:10 dilutions according to conventional procedures by using 0.05% trypsin plus 0.02% EDTA in a HEPES buffered salt solution (see Shipman, C., Jr.; Smith, S. H.; Carlson, R. H.; Drach, J. C. Antiviral Activity of Arabinofuranosyladenine and Arabinofuranosylhypoxanthine in Herpes Simplex Virus-Infected KB Cells. I. Selective Inhibition of Viral DNA Synthesis in Synchronized Suspension Cultures. *Antimicrob. Agents Chemother.* 1976, 9, 120–127).

Virological Procedures

Stock HCMV was prepared by infecting HFF cells at a multiplicity of infection (m.o.i.) of <0.01 plaque-forming units (p.f.u.) per cell as detailed previously (see Turk, S. R.; Shipman, C., Jr.; Nassiri, M. R.; Genzingler, G.; Krawczyk, S. H.; Townsend, L. B.; Drach, J. C. Pyrrolo[2,3-d] pyrimidine Nucleosides as Inhibitors of Human Cytomegalovirus, *Antimicrob. Agents Chemother.* 1987, 31, 544–550). High titer HSV-1 stocks were prepared by infecting KB cells (ATCC) at an m.o.i. of <0.1 also as detailed previously (see Turk, S. R.; Shipman, C., Jr.; Nassiri, M. R.; Genzingler, G.; Krawczyk, S. H.; Townsend, L. B.; Drach, J. C. Pyrrolo[2,3-d]pyrimidine Nucleosides as Inhibitors of Human Cytomegalovirus, *Antimicrob. Agents Chemother.* 1987, 31, 544–550). Virus titers were determined using monolayer cultures of HFF cells for HCMV and monolayer cultures of BSC-1 cells for HSV-1 as described earlier (see Prichard, M. N.; Turk, S. R.; Coleman, L. A.; Engelhardt, S. L.; Shipman, C., Jr.; Drach, J. C. A Microtiter Virus Yield Reduction Assay for the Evaluation of Antiviral Compounds Against Human Cytomegalovirus and Herpes Simplex Virus. *J. Virol. Methods* 1990, 28, 101–106). Briefly, HFF or BSC-1 cells were planted as described above in 96-well cluster dishes and incubated overnight at 37° C. The next day cultures were inoculated with HCMV or HSV-1 and serially diluted 1:3 across the remaining eleven columns of the 96-well plate. After virus adsorption the inoculum was replaced with fresh medium and cultures were incubated for seven days for HCMV, two or three days for HSV-1. Plaques were enumerated under 20-fold magnification in wells having the dilution which gave 5 to 20 plaques per well. Virus titers were calculated according to the following formula: Titer (p.f.u./mL)=number of plaques×5×3$^n$; where n represents the nth dilution of the virus used to infect the well in which plaques were enumerated.

HCMV Plaque Reduction Assay

HFF cells in 24-well cluster dishes were infected with approximately 100 p.f.u. of HCMV per cm$^2$ cell sheet using the procedures detailed above. Following virus adsorption, compounds dissolved in growth medium were added to duplicate wells in four to eight selected concentrations. After incubation at 37° C. for 7 to 10 days, cell sheets were fixed, stained with crystal violet and microscopic plaques enumerated as described above. Drug effects were calculated as a percentage of reduction in number of plaques in the presence of each drug concentration compared to the number observed in the absence of drug.

HCMV Yield Assay

HFF cells were planted as described above in 96-well cluster dishes, incubated overnight, medium removed and the cultures were inoculated with HCMV at a m.o.i. of 0.5 to 1 p.f.u. per cell as reported elsewhere (see Prichard, M. N.; Turk, S. R.; Coleman, L. A.; Engelhardt, S. L.; Shipman, C., Jr.; Drach, J. C. A Microtiter Virus Yield Reduction Assay for the Evaluation of Antiviral Compounds Against Human Cytomegalovirus and Herpes Simplex Virus. *J. Virol. Methods* 1990, 28, 101–106). After virus adsorption, inoculum was replaced with 0.2 mL of fresh medium containing test compounds. The first row of 12 wells was left undisturbed and served as virus controls. Each well in the second row received an additional 0.1 mL of medium with test compound at three times the desired final concentration. The contents of the 12 wells were mixed by repeated pipetting and then serially diluted 1:3 along the remaining wells. In this manner, six compounds could be tested in duplicate on a single plate with concentrations from 100 mM to 0.14 mM. Plates were incubated at 37° C. for seven days, subjected to one cycle of freezing and thawing; aliquots from each of the eight wells of a given column were transferred to the first column of a fresh 96-well monolayer culture of HFF cells. Contents were mixed and serially diluted 1:3 across the remaining eleven columns of the secondary plate. Each column of the original primary plate was diluted across a separate plate in this manner. Cultures were incubated, plaques were enumerated, and titers calculated as described above.

HSV-1 ELISA

An ELISA was employed (see Prichard, M. N.; Shipman, C., Jr. A Three Dimensional Model to Analyze Drug-Drug Interactions. *Antiviral Res.* 1990, 14, 181–206) to detect HSV-1. Ninety-six-well cluster dishes were planted with 10,000 BSC-1 cells per well in 200 μL per well of MEM(E) plus 10% calf serum. After overnight incubation at 37° C., selected drug concentrations in quadruplicate and HSV-1 at a concentration of 100 p.f.u./well were added. Following a 3-day incubation at 37° C., medium was removed, plates were blocked, rinsed, and horse radish peroxidase conjugated rabbit anti-HSV-1 antibody was added. Following removal of the antibody containing solution, plates were rinsed, and then developed by adding 150 μL per well of a solution of tetramethylbenzidine as substrate. The reaction was stopped with $H_2SO_4$ and absorbance was read at 450 and 570 nm. Drug effects were calculated as a percentage of the reduction in absorbance in the presence of each drug concentration compared to absorbance obtained with virus in the absence of drug.

HHV-6 (ELISA)

An enzyme-linked immunosorbent assay (ELISA) is performed in covalent amine plates (Costar, Cambridge, Mass.). The plates are activated by the addition of a homobifunctional crosslinking agent, bis(sulfosuccinimidyl) suberate and then washed with PBS. Samples consisting of 150 μl of suspended HSB2 cells are infected with HHV-6 and previously incubated with drug on a separate plate are solubilized in Triton X-100 in coating buffer. The plate is covered and incubated for 1 hour at 37° C. in a 5% $CO_2$ atmosphere. These binding conditions facilitated covalent attachment of the antigen to the free end of the crosslinker. After covalent binding, the antigen solution is decanted and the plate is washed six times in HEPES buffered saline (see Shipman, C., Jr., Evaluation of 4-(2-Hydroxyethyl)-1-piperazineethane-sulfonic Acid (HEPES) as a Tissue Culture Buffer, *Proc. Soc. Exp. Biol.* 1969, 130, 305–310) with 0.05% Tween 20 (HBS-T), and soaked for three minutes for each wash. Unbound sites on the plate are blocked, the blocker decanted, and diluted primary monoclonal antibody, specific for HHV-6 (GS) is added. The plate is then covered and incubated for 1 hour at 37° C. The plate is washed again, blocker is added again, and horse radish peroxidase-labeled rabbit anti-mouse antibody added to each well. The plate is incubated for 1 hour at 37° C., washed again as described above, and developed using TMB-Turbo (Pierce, Rockford, Ill.) for 30 minutes at room temperature. The reaction is stopped with 2 M $H_2SO_4$. Absorbance in each well is determined at 450/570 nanometers.

HIV-1

This assay measures the presence of HIV in supernatants of CEM cells (ATCC) infected with strain IIIB of HIV-1 by the amount of RT activity. Reverse transcriptase (RT) is employed as a marker for HIV-1. Cells are grown, infected, and incubated in the presence of seven concentrations (one-half log 10 dilutions) beginning at 1 or 100 $\mu$M of compounds to be assayed. Procedures and the RT assay are performed as detailed in Kucera, L. S., Iyer, N., Puckett, S. H., Buckheit, R. W., Jr., Westbrook, L., Toyer, B. R., White, E. L., Germany-Decker, J. M., Shannon, W. M., Chen, R. C. S., Nassiri, M. R. S., Shipmen, C., Jr., Townsend, L. B., Drach, J. C., Activity of Triciribine and Triciribine-5'-monophosphate Against Human Immunodeficiency Virus Types 1 and 2, *AIDS Res. Human Retroviruses* 1993, 9, 307–314; White, E. L., Buckheit, R. W., Jr., Ross, L. J., Germany, J. M., Andries, K., Pauwels, R., Janssen, P. A. J., Shannon, W. M., Chirigosm, M. A., A TIBO Derivative, R82913, is a Potent Inhibitor of HIV-1 Reverse Transcriptase with Heteropolymer Templates, *Antiviral Res.* 1991, 16, 257–266.

Cytotoxicity Assays

Two different assays were used for routine cytotoxicity testing. (i) Cytotoxicity produced in stationary HFF cells was determined by microscopic inspection of cells not affected by the virus used in plaque assays (see Turk, S. R.; Shipman, C., Jr.; Nassiri, M. R.; Genzingler, G.; Krawczyk, S. H.; Townsend, L. B.; Drach, J. C. Pyrrolo[2,3-]pyrimidine Nucleosides as Inhibitors of Human Cytomegalovirus, *Antimicrob. Agents Chemother.* 1987, 31, 544–550). (ii) The effect of compounds during two population doublings of KB cells was determined by crystal violet staining and spectrophotometric quantitation of dye eluted from stained cells as described earlier (see Prichard, M. N.; Prichard, L. E., Baguley, W. A.; Nassiri, M. R.; Shipman, C., Jr. Three-Dimensional Analysis of the Synergistic Cytotoxicity of Ganciclovir and Zidovudine. *Antiviral Res.* 1991, 35, 1060–1065). Briefly, 96-well cluster dishes were planted with KB cells at 3000–5000 cells per well. After overnight incubation at 37° C., test compound was added in quadruplicate at six to eight concentrations. Plates were incubated at 37° C. for 48 hours in a $CO_2$ incubator, rinsed, fixed with 95% ethanol, and stained with 0.1% crystal violet. Acidified ethanol was added and plates read at 570 nm in a spectrophotometer designed to read 96-well ELISA assay plates.

Data Analysis

Dose-response relationships were constructed by linearly regressing the percent inhibition of parameters derived in the preceding sections against log drug concentrations. Fifty-percent inhibitory concentrations ($IC_{50}$'s) or $IC_{90}$'s were calculated from the regression lines. Samples containing positive controls (acyclovir for HSV-1, ganciclovir for HCMV, and 2-acetylpyridine thiosemicarbazone for cytotoxicity) were used in all assays. Antiviral activity data for HCMV (plaque and yield) and HSV-1 (ELISA) and cytotoxicity data (visual and growth) were recorded for many of the compounds synthesized. The data are summarized in Table 2. Antiviral activity data for another HCMV strain, AD169, were also recorded for many of the compounds synthesized. The data are summarized in Table 3.

TABLE 2

Antiviral Activity and Cytotoxicity Data

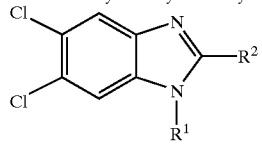

| | | | | 50% or 90% Inhibitory Concentration ($\mu$M) | | | | |
|---|---|---|---|---|---|---|---|---|
| | | | | Antiviral Activity | | | | |
| | | | | HCMV[a] | | HSV-1[b] | Cytotoxicity[c] | |
| Cmpd | $R^2$ | $R^1$ | isomer | plaque | yield | ELISA | visual[d] | growth |
| 4a | Cl | α-lyxose | L | 18 | 3.4 | >100 | 190 | >100 |
| 4b | Cl | α-lyxose | D | 18 | >100[d] | 90 | >100 | >100 |
| 5a | Br | α-lyxose | L | 2.8[d] | 0.8[d] | >100[e] | >100 | >100 |
| 5b | Br | α-lyxose | D | 6 | 65[d] | 50 | >100 | >100 |
| 6a | $NHCH_3$ | α-lyxose | L | >100 | — | >100 | >100 | >100 |
| 6b | $NHCH_3$ | α-lyxose | D | >100 | >100 | >100 | >100 | >100 |
| 7a | $NHC_3H_7$ | α-lyxose | L | >100 | 19 | >100 | >100 | >100 |
| 7b | $NHC_3H_7$ | α-lyxose | D | 60 | 17 | >100 | >100 | >100 |
| 8a | $NHC_3H_5$ | α-lyxose | L | >100 | 35[d] | >100 | >100 | >100 |
| 8b | $NHC_3H_5$ | α-lyxose | D | >100[d] | 70 | >100 | >100 | >100 |
| 9a | SH | α-lyxose | L | >100 | >100 | >100 | >100 | >100 |

TABLE 2-continued

Antiviral Activity and Cytotoxicity Data (structure: 5,6-dichlorobenzimidazole with R² at 2-position and R¹ on N)

| | | | | 50% or 90% Inhibitory Concentration ($\mu$M) | | | | |
|---|---|---|---|---|---|---|---|---|
| | | | | Antiviral Activity | | | Cytotoxicity[c] | |
| | | | | HCMV[a] | | HSV-1[b] | | |
| Cmpd | R² | R¹ | isomer | plaque | yield | ELISA | visual[d] | growth |
| 9b | SH | α-lyxose | D | >100 | >100 | >100 | >100 | >100 |
| 11a | SCH₂C₆H₅ | α-lyxose | L | 32 | 17 | 60 | 32 | 40 |
| 11b | SCH₂C₆H₅ | α-lyxose | D | 32 | 15 | 55 | 32 | 60 |
| 12a | SCH₃ | α-lyxose | L | >100 | — | >100 | >100 | >100 |
| 12b | SCH₃ | α-lyxose | D | >100 | >100 | >100 | >100 | >100 |
| foscarnet[f] | | | | 39 ± 26 | — | — | >100 | — |
| ganciclovir (DHPG)[g] | | | | 7.4 ± 6.5 | 1.6 ± 1.2 | 3.5 ± 2.1 | >100 | >100 |

[a]plaque and yield reduction assays were performed in duplicate as described in the text. Results from plaque assays are reported as $IC_{50}$'s, those for yield reduction experiments as $IC_{90}$'s.
[b]The plaque assay was used to determine the activity of DHPG against HSV-1; all other compounds were assayed by ELISA in quadruplicate wells.
[c]Visual cytotoxicity was scored on HFF cells at time of HCMV plaque enumeration. Results of duplicate experiments presented. Inhibition of KB cell growth was determined as described in the text in quadruplicate assays. Results are presented as $IC_{50}$'s.
[d]Average derived from two to four experiments.
[e]>100 indicates $IC_{50}$ or $IC_{90}$ greater than the noted (highest) concentration tested.
[f]Average ± standard deviation from 15 experiments.
[g]Average ± standard deviation from 108, 33, and 3 experiments, respectively.

TABLE 3

Antiviral Activity and Cytotoxicity Data (structure: 5,6-dichlorobenzimidazole with R² at 2-position and R¹ on N)

| | | | | 50 or 90% Inhibitory Concentration ($\mu$m) HCMV Strain | | |
|---|---|---|---|---|---|---|
| | | | | Towne[a] | | AD169 |
| Cmpd | R² | R¹ | isomer | plaque | yield | plaque |
| TCRB | Cl | β-ribose | D | 2.9 | 1.4 | 1.8 |
| 4a | Cl | α-lyxose | L | 18 | 3.4 | 2.6 |
| 4b | Cl | α-lyxose | D | 18 | >100[b] | 9 |
| 5a | Br | α-lyxose | L | 2.8 | 0.8 | 0.8 |
| 5b | Br | α-lyxose | D | 6 | 65[b] | 4.2 |
| 7a | NHC₃H₇ | α-lyxose | L | >100 | 19 | 11 |
| 7b | NHC₃H₇ | α-lyxose | D | 60 | 17 | 32 |
| 8a | NHC₃H₅ | α-lyxose | L | >100 | 35 | 160 |
| 8b | NHC₃H₅ | α-lyxose | D | >100[b] | 70 | >100 |
| 11a | SCH₂C₆H₅ | α-lyxose | L | 32 | 17 | 32 |
| 11b | SCH₂C₆H₅ | α-lyxose | D | 32 | 15 | 32 |

[a]Plaque and yield reduction assays were performed in duplicate as described in the text. Data for Towne strain also presented in Table 2. Results from plaque assays are reported as $IC_{50}$'s, those for yield reduction experiments as $IC_{90}$'s.
[b]Average derived from two or three experiments.

The activity of compounds against Hepatitis B Virus (HBV) was assessed as described in Jansen, R., et al., Antimicrobial Agents and Chemotherapy, Vol. 37, No. 3, pp. 441–447, 1993. The $IC_{50}$ values for 2-bromo-5,6-dichloro-1-(α-L-lyxofuranosyl)benzimidazole (compound 5a) in two separate tests were 8.8 $\mu$M and 16 $\mu$M.

While the invention has been described in detail and with reference to specific embodiments thereof, it will be apparent to one skilled in the art that various changes and modifications can be made therein without departing from the spirit and scope thereof.

What is claimed is:

1. A L-lyxofuranosyl benzimidazole compound selected from the group consisting of:

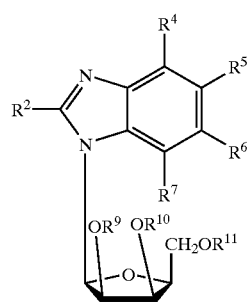

(beta-L)

-continued and

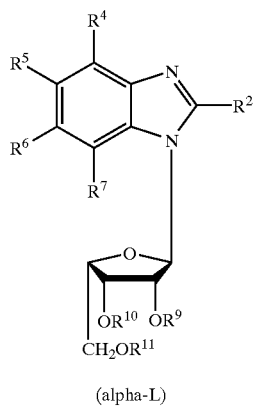

(alpha-L)

wherein $R^2$, $R^4$, $R^5$, $R^6$, and $R^7$ are independently the same or different and independently selected from the group consisting of: —H, —F, —Cl, —Br, —I, —NO$_2$, —N(R$^8$)$_2$, —OR$^8$, —SR$^{12}$, and —CF$_3$, wherein $R^8$ is independently —H or an alkyl group having 1–6 carbon atoms and wherein $R^{12}$ is independently —H or a hydrocarbyl group having 1–10 carbon atoms; and, $R^9$, $R^{10}$ and $R^{11}$ are independently the same or different and are H or a hydroxyl protecting group; and pharmaceutically acceptable salts thereof.

2. A L-lyxofuranosyl benzimidazole compound according to claim 1, wherein:

$R^2$ is selected from the group consisting of: —H, —F, —Cl, —Br, —I, and —N(R$^8$)$_2$;

$R^4$ and $R^7$ are both —H;

$R^5$ and $R^6$ are independently selected from the group consisting of: —H, —F, —Cl, —Br, and —I.

3. A D-lyxofuranosyl benzimidazole compound selected from the group consisting of:

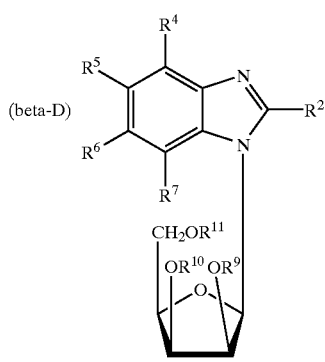

(beta-D)

-continued

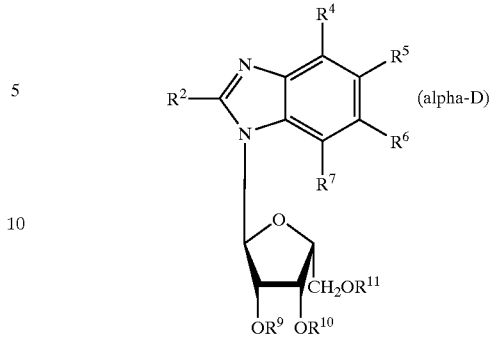

(alpha-D)

wherein $R^2$ is selected from the group consisting of —F, —Cl, —Br, —I, —NH$_2$, —NHR, —N(R)$_2$, —SH, and —SR' wherein R is an alkyl group having 1–6 carbon atoms and R' is a hydrocarbyl group having 1–10 carbon atoms;

$R^4$, $R^5$, $R^6$, and $R^7$ are independently the same or different and independently selected from the group consisting of: —H, —F, —Cl, —Br, —I, —NO$_2$, —N(R$^8$)$_2$, —OR$^8$, —SR$^{12}$, and —CF$_3$, wherein $R^8$ is independently —H or an alkyl group having 1–6 carbon atoms and wherein $R^{12}$ is independently —H or a hydrocarbyl group having 1–10 carbon atoms; and, $R^9$, $R^{10}$ and $R^{11}$ are independently the same or different and are H or a hydroxyl protecting group;

optical isomers thereof; and pharmaceutically acceptable salts thereof.

4. A D-lyxofuranosyl benzimidazole compound according to claim 3, wherein:

$R^4$ and $R^7$ are both —H; and $R^5$ and $R^6$ are independently selected from the group consisting of: —H, —F, —Cl, —Br, and —I.

5. A L-lyxofuranosyl benzimidazole compound according to claim 1, wherein said compound is a α-L-lyxofuranosyl benzimidazole compound.

6. A L-lyxofuranosyl benzimidazole compound according to claim 1, wherein said compound is a β-L-lyxofuranosyl benzimidazole compound.

7. A D-lyxofuranosyl benzimidazole compound according to claim 3, wherein said compound is a α-D-lyxofuranosyl benzimidazole compound.

8. A D-lyxofuranosyl benzimidazole compound according to claim 3, wherein said compound is a β-D-lyxofuranosyl benzimidazole compound.

9. A L-lyxofuranosyl benzimidazole compound according to claim 2, wherein said compound is a α-L-lyxofuranosyl benzimidazole compound.

10. A L-lyxofuranosyl benzimidazole compound according to claim 2, wherein said compound is a β-L-lyxofuranosyl benzimidazole compound.

11. A L-lyxofuranosyl benzimidazole compound according to claim 1, selected from the group consisting of:

1-(lyxofuranosyl)-2,5,6-trichloro-benzimidazole;

1-(lyxofuranosyl)-2-bromo-5,6-dichloro-benzimidazole;

1-(lyxofuranosyl)-2-methylamino-5,6-dichloro-benzimidazole;

1-(lyxofuranosyl)-2-isopropylamino-5,6-dichloro-benzimidazole;

1-(lyxofuranosyl)-2-cyclopropylamino-5,6-dichloro-benzimidazole;

1-(lyxofuranosyl)-2-thio-5,6-dichloro-benzimidazole;

1-(lyxofuranosyl)-2-benzylthio-5,6-dichloro-benzimidazole;

1-(lyxofuranosyl)-2-methylthio-5,6-dichloro-benzimidazole;

and pharmaceutically acceptable salts thereof.

12. A L-lyxofuranosyl benzimidazole compound according to claim 1, selected from the group consisting of:

1-(lyxofuranosyl)-2,5,6-trichloro-benzimidazole;

and pharmaceutically acceptable salts thereof.

13. A L-lyxofuranosyl benzimidazole compound according to claim 1, selected from the group consisting of:

1-(lyxofuranosyl)-2-bromo-5,6-dichloro-benzimidazole;

and pharmaceutically acceptable salts thereof.

14. A L-lyxofuranosyl benzimidazole compound according to claim 1, selected from the group consisting of:

1(lyxofuranosyl)-2-methylamino-5,6-dichloro-benzimidazole;

and pharmaceutically acceptable salts thereof.

15. A L-lyxofuranosyl benzimidazole compound according to claim 1, selected from the group consisting of:

1-(lyxofuranosyl)-2-isopropylamino-5,6-dichloro-benzimidazole;

and pharmaceutically acceptable salts thereof.

16. A L-lyxofuranosyl benzimidazole compound according to claim 1, selected from the group consisting of:

1-(lyxofuranosyl)-2-cyclopropylamino-5,6-dichloro-benzimidazole;

and pharmaceutically acceptable salts thereof.

17. A L-lyxofuranosyl benzimidazole compound according to claim 1, selected from the group consisting of:

1-(lyxofuranosyl)-2-thio-5,6-dichloro-benzimidazole;

and pharmaceutically acceptable salts thereof.

18. A L-lyxofuranosyl benzimidazole compound according to claim 1, selected from the group consisting of:

1-(lyxofuranosyl)-2-benzylthio-5,6-dichloro-benzimidazole;

and pharmaceutically acceptable salts thereof.

19. A L-lyxofuranosyl benzimidazole compound according to claim 1, selected from the group consisting of:

1-(lyxofuranosyl)-2-methylthio-5,6-dichloro-benzimidazole;

and pharmaceutically acceptable salts thereof.

20. A pharmaceutical composition comprising a pharmaceutically acceptable carrier and a L-lyxofuranosyl benzimidazole compound according to claim 1.

21. A method for preventing or inhibiting herpes viral propagation and/or replication in a herpes virally-infected cell comprising contacting the cell with an effective amount of a L-lyxofuranosyl benzimidazole compound according to claim 1, to prevent or inhibit herpes viral propagation and/or replication in the cell.

22. The method according to claim 21, wherein the herpes viral infection is selected from the group consisting of HCMV, HSV-1, HSV-2, VZV, EBV, HHV-6, HHV-7, and HHV-8.

23. A method for preventing or inhibiting viral propagation and/or replication of a viral infection selected from the group consisting of hepatitis B and hepatitis C, in a virally-infected cell, said method comprising contacting the cell with an effective amount of a L-lyxofuranosyl benzimidazole compound according to claim 1, to prevent or inhibit viral propagation and/or replication in the cell.

24. A method for preventing a herpes viral infection in a cell comprising contacting the cell with a prophylactically effective amount of a L-lyxofuranosyl benzimidazole compound according to claim 1.

25. The method according to claim 24, wherein the viral infection is selected from the group consisting of HCMV, HSV-1, HSV-2, VZV, EBV, HHV-6, HHV-7, and HHV-8.

26. A method for preventing a hepatitis B or hepatitis C viral infection in a cell comprising contacting the cell with a prophylactically effective amount of a L-lyxofuranosyl benzimidazole compound according to claim 1.

27. A method for treating a herpes viral infection comprising administering to an infected host a therapeutically effective amount of a L-lyxofuranosyl benzimidazole compound according to claim 1.

28. The method according to claim 27, wherein the herpes viral infection is selected from the group consisting of HCMV, HSV-1, HSV-2, VZV, EBV, HHV-6, HHV-7, and HHV-8.

29. A method for treating a hepatitis B or hepatitis C viral infection comprising administering to an infected host a therapeutically effective amount of a L-lyxofuranosyl benzimidazole compound according to claim 1.

30. A method for preventing a herpes viral infection in a host comprising administering to the host a prophylactically effective amount of a L-lyxofuranosyl benzimidazole compound according to claim 1.

31. The method according to claim 30, wherein the herpes viral infection is selected from the group consisting of HCMV, HSV-1, HSV-2, VZV, EBV, HHV-6. HHV-7, and HHV-8.

32. A method for preventing a hepatitis B or hepatitis C viral infection in a host comprising administering to the host a prophylactically effective amount of a L-lyxofuranosyl benzimidazole compound according to claim 1.

33. A process for the preparation of a L-lyxofuranosyl benzimidazole compound according to claim 1, said process comprising the steps of:

(a) reacting a compound of formula (II) with a L-lyxose compound of formula (III),

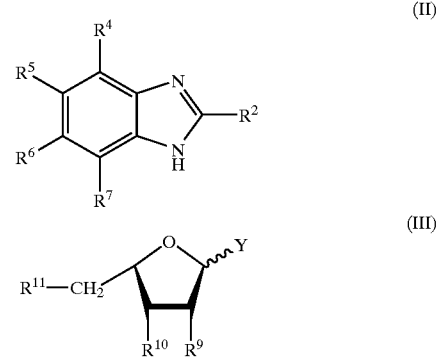

wherein $R^2$ is selected from the group consisting of —Cl, —Br and =S, and each of $R^9$, $R^{10}$ or $R^{11}$ is a hydroxyl protecting group to obtain an intermediate product of the following formula

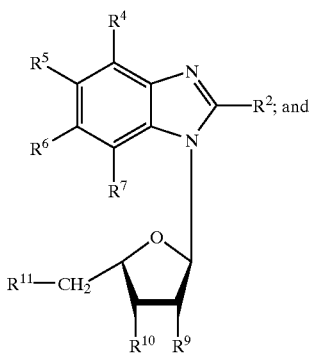

and (b) subsequently performing one or more of the following steps:
  (i) removing one or more hydroxyl protecting groups from the product of (a);
  (ii) reacting the product of (a) with HX, wherein X is selected from the group consisting of —Cl, —Br, and —I;
  (iii) reacting the product of (a) with $R^8NH_2$, wherein $R^8$ is —H or a linear, branched, or cyclic alkyl group having 1–6 carbon atoms;
  (iv) reacting the product of (a) with $H_2NCSNH_2$;
  (v) reacting the product of (a) with $C_6H_5CH_2X$, wherein X is selected from the group consisting of —Cl, —Br, and —I;
  (vi) reacting the product of (b)(iv) with $C_6H_5CH_2X$, wherein X is selected from the group consisting of —Cl, —Br, and —I;
  (vii) reacting the product of (a) with $CH_3I$; and,
  (viii) reacting the product of (b)(iv) with $CH_3I$ to obtain L-lyxofuranosyl benzimidazole compound selected from the group consisting of:

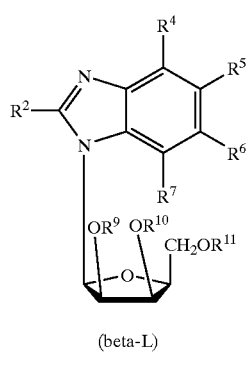

(beta-L)

and

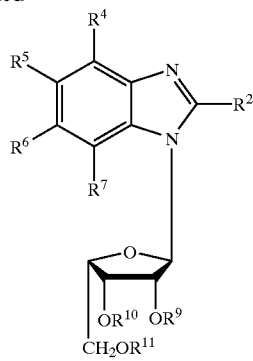

(alpha-L)

34. The method according to claim 23, wherein the hepatitis B or hepatitis C viral infection is a hepatitis B viral infection.

35. The method according to claim 26, wherein the hepatitis B or hepatitis C viral infection is a hepatitis B viral infection.

36. The method according to claim 29, wherein the hepatitis B or hepatitis C viral infection is a hepatitis B viral infection.

37. The method according to claim 32, wherein the hepatitis B or hepatitis C viral infection is a hepatitis B viral infection.

38. A D-lyxofuranosyl benzimidazole compound according to claim 4, wherein said compound is a β-D-lyxofuranosyl benzimidazole compound.

39. A D-lyxofuranosyl benzimidazole compound according to claim 4, wherein said compound is a β-D-lyxofuranosyl benzimidazole compound.

40. A D-lyxofuranosyl benzimidazole compound according to claim 3, selected from the group consisting of:
  1-(lyxofuranosyl)-2,5,6-trichloro-benzimidazole;
  1-(lyxofuranosyl)-2-bromo-5,6-dichloro-benzimidazole;
  1-(lyxofuranosyl)-2-methylamino-5,6-dichloro-benzimidazole;
  1-(lyxofuranosyl)-2-isopropylamino-5,6-dichloro-benzimidazole;
  1-(lyxofuranosyl)-2-cyclopropylamino-5,6-dichloro-benzimidazole;
  1-(lyxofuranosyl)-2-thio-5,6-dichloro-benzimidazole;
  1-(lyxofuranosyl)-2-benzylthio-5,6-dichloro-benzimidazole;
  1-(lyxofuranosyl)-2-methylthio-5,6-dichloro-benzimidazole;
  optical isomers thereof; and pharmaceutically acceptable salts thereof.

41. A D-lyxofuranosyl benzimidazole compound according to claim 3, selected from the group consisting of:
  1-(lyxofuranosyl)-2,5,6-trichloro-benzimidazole;
  optical isomers thereof; and pharmaceutically acceptable salts thereof.

42. A D-lyxofuranosyl benzimidazole compound according to claim 3, selected from the group consisting of:
  1-(lyxofuranosyl)-2-bromo-5,6-dichloro-benzimidazole;
  optical isomers thereof; and pharmaceutically acceptable salts thereof.

43. A D-lyxofuranosyl benzimidazole compound according to claim 3, selected from the group consisting of:
1(lyxofuranosyl)-2-methylamino-5,6-dichloro-benzimidazole;
optical isomers thereof; and pharmaceutically acceptable salts thereof.

44. A D-lyxofuranosyl benzimidazole compound according to claim 3, selected from the group consisting of:
1-(lyxofuranosyl)-2-isopropylamino-5,6-dichloro-benzimidazole;
optical isomers thereof; and pharmaceutically acceptable salts thereof.

45. A D-lyxofuranosyl benzimidazole compound according to claim 3, selected from the group consisting of:
1-(lyxofuranosyl)-2-cyclopropylamino-5,6-dichloro-benzimidazole;
optical isomers thereof; and pharmaceutically acceptable salts thereof.

46. A D-lyxofuranosyl benzimidazole compound according to claim 3, selected from the group consisting of:
1-(lyxofuranosyl)-2-thio-5,6-dichloro-benzimidazole;
optical isomers thereof; and pharmaceutically acceptable salts thereof.

47. A D-lyxofuranosyl benzimidazole compound according to claim 3, selected from the group consisting of:
1-(lyxofuranosyl)-2-benzylthio-5,6-dichloro-benzimidazole;
optical isomers thereof; and pharmaceutically acceptable salts thereof.

48. A D-lyxofuranosyl benzimidazole compound according to claim 3, selected from the group consisting of:
1-(lyxofuranosyl)-2-methylthio-5,6-dichloro-benzimidazole;
optical isomers thereof; and pharmaceutically acceptable salts thereof.

49. A pharmaceutical composition comprising a pharmaceutically acceptable carrier and a D-lyxofuranosyl benzimidazole compound according to claim 3.

50. A method for preventing or inhibiting herpes viral propagation and/or replication in a herpes virally-infected cell comprising contacting the cell with an effective amount of a D-lyxofuranosyl benzimidazole compound according to claim 3, to prevent or inhibit herpes viral propagation and/or replication in the cell.

51. The method according to claim 50, wherein the herpes viral infection is selected from the group consisting of HCMV, HSV-1, HSV-2, VZV, EBV, HHV-6, HHV-7, and HHV-8.

52. A method for preventing or inhibiting viral propagation and/or replication of a viral infection selected from the group consisting of hepatitis B and hepatitis C, in a virally-infected cell, said method comprising contacting the cell with an effective amount of a D-lyxofuranosyl benzimidazole compound according to claim 3, prevent or inhibit viral propagation and/or replication in the cell.

53. The method according to claim 52, wherein the hepatitis B or hepatitis C viral infection is a hepatitis B viral infection.

54. A method for preventing a herpes viral infection in a cell comprising contacting the cell with a prophylactically effective amount of a D-lyxofuranosyl benzimidazole compound according to claim 3.

55. The method according to claim 54, wherein the herpes viral infection is selected from the group consisting of HCMV, HSV-1, HSV-2, VZV, EBV, HHV-6, HHV-7, and HHV-8.

56. A method for preventing a hepatitis B or hepatitis C viral infection in a cell comprising contacting the cell with a prophylactically effective amount of a D-lyxofuranosyl benzimidazole compound according to claim 3.

57. The method according to claim 56, wherein the hepatitis B or hepatitis C viral infection is a hepatitis B viral infection.

58. A method for treating a herpes viral infection comprising administering to an infected host a therapeutically effective amount of a D-lyxofuranosyl benzimidazole compound according to claim 3.

59. The method according to claim 58, wherein the herpes viral infection is selected from the group consisting of HCMV, HSV-1, HSV-2, VZV, EBV, HHV-6, HHV-7, and HHV-8.

60. A method for treating a hepatitis B or hepatitis C viral infection comprising administering to an infected host a therapeutically effective amount of a D-lyxofuranosyl benzimidazole compound according to claim 3.

61. The method according to claim 60, wherein the hepatitis B or hepatitis C viral infection is a hepatitis B viral infection.

62. A method for preventing a herpes viral infection in a host comprising administering to the host a prophylactically effective amount of a D-lyxofuranosyl benzimidazole compound according to claim 3.

63. The method according to claim 62, wherein the herpes viral infection is selected from the group consisting of HCMV, HSV-1, HSV-2, VZV, EBV, HHV-6, HHV-7, and HHV-8.

64. A method for preventing a hepatitis B or hepatitis C viral infection in a host comprising administering to the host a prophylactically effective amount of a D-lyxofuranosyl benzimidazole compound according to claim 3.

65. The method according to claim 64, wherein the hepatitis B or hepatitis C viral infection is a hepatitis B viral infection.

66. A process for the preparation of a D-lyxofuranosyl benzimidazole compound according to claim 3, said process comprising the steps of:

(c) reacting a compound of formula (II) with a D-lyxose compound of formula (III),

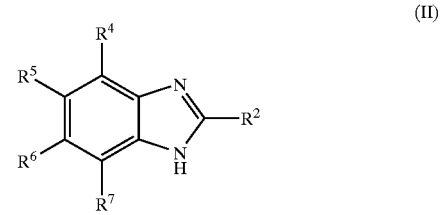

-continued

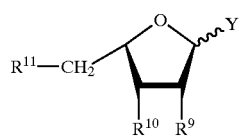
(III)

wherein $R^2$ is selected from the group consisting of —Cl, —Br and =S, and
each of $R^9$, $R^{10}$ or $R^{11}$ is a hydroxyl protecting group; and, (d) subsequently performing one or more of the following steps:
  (ix) removing one or more hydroxyl protecting groups from the product of (a);
  (x) reacting the product of (a) with HX, wherein X is selected from the group consisting of —Cl, —Br, and —I;
  (xi) reacting the product of (a) with $R^8NH_2$, wherein $R^8$ is —H or a linear, branched, or cyclic alkyl group having 1–6 carbon atoms;
  (xii) reacting the product of (a) with $H_2NCSNH_2$;
  (xiii) reacting the product of (a) with $C_6H_5CH_2X$, wherein X is selected from the group consisting of —Cl, —Br, and —I;
  (xiv) reacting the product of (b)(iv) with $C_6H_5CH_2X$, wherein X is selected from the group consisting of —Cl, —Br, and —I;
  (xv) reacting the product of (a) with $CH_3I$; and,
  (xvi) reacting the product of (b)(iv) with $CH_3I$ to obtain a D-lyxofuranosyl benzimidazole compound selected from the group consisting of:

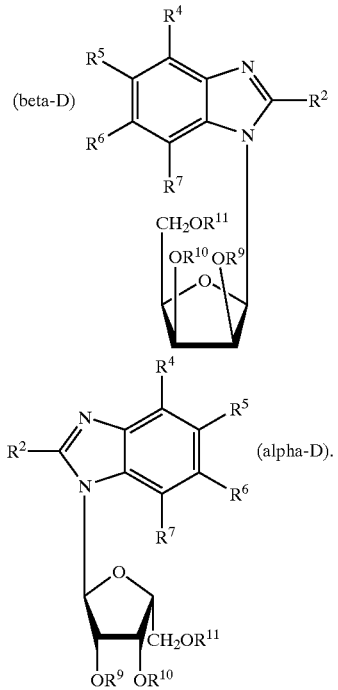

\* \* \* \* \*

UNITED STATES PATENT AND TRADEMARK OFFICE
CERTIFICATE OF CORRECTION

| | | |
|---|---|---|
| PATENT NO. | : 6,455,506 B1 | Page 1 of 1 |
| APPLICATION NO. | : 09/124484 | |
| DATED | : September 24, 2002 | |
| INVENTOR(S) | : Townsend et al. | |

It is certified that error appears in the above-identified patent and that said Letters Patent is hereby corrected as shown below:

On Title Page Under (75) Inventors: please add --Karen K. Biron, Apex, NC (US); and Frank L. Boyd, Jr., Raleigh, NC (US)--

Signed and Sealed this

Twenty-eighth Day of November, 2006

JON W. DUDAS
*Director of the United States Patent and Trademark Office*